(12) United States Patent
Kim et al.

(10) Patent No.: US 9,775,914 B2
(45) Date of Patent: Oct. 3, 2017

(54) PRODRUGS ACTIVATED BY CASPASE

(71) Applicant: PHAROSGEN CO., LTD., Seoul (KR)

(72) Inventors: Sang-Yoon Kim, Seoul (KR); Youngro Byun, Seoul (KR); Seung Woo Chung, Kyunggi-do (KR)

(73) Assignee: PHAROSGEN CO., LTD., Seoul (KR)

( * ) Notice: Subject to any disclaimer, the term of this patent is extended or adjusted under 35 U.S.C. 154(b) by 0 days.

(21) Appl. No.: 14/796,219

(22) Filed: Jul. 10, 2015

(65) Prior Publication Data

US 2016/0144050 A1    May 26, 2016

Related U.S. Application Data

(60) Provisional application No. 62/114,126, filed on Feb. 10, 2015.

(30) Foreign Application Priority Data

Nov. 20, 2014  (KR) ........................ 10-2014-0162555

(51) Int. Cl.
| | |
|---|---|
| *A61K 47/48* | (2006.01) |
| *A61K 31/65* | (2006.01) |
| *A61K 31/337* | (2006.01) |
| *A61K 45/06* | (2006.01) |
| *A61N 1/40* | (2006.01) |
| *A61K 38/14* | (2006.01) |
| *A61B 18/02* | (2006.01) |
| *A61N 7/00* | (2006.01) |
| *A61N 5/067* | (2006.01) |
| *A61N 5/06* | (2006.01) |
| *A61N 7/02* | (2006.01) |

(52) U.S. Cl.
CPC ...... *A61K 47/48338* (2013.01); *A61K 31/337* (2013.01); *A61K 31/65* (2013.01); *A61K 38/14* (2013.01); *A61K 45/06* (2013.01); *A61K 47/4823* (2013.01); *A61K 47/48038* (2013.01); *A61K 47/48061* (2013.01); *A61K 47/48107* (2013.01); *A61K 47/48215* (2013.01); *A61K 47/48284* (2013.01); *A61N 1/403* (2013.01); *A61B 18/02* (2013.01); *A61N 5/062* (2013.01); *A61N 7/02* (2013.01); *A61N 2005/067* (2013.01); *A61N 2007/0004* (2013.01)

(58) Field of Classification Search
CPC ........ A61K 47/48138; A61K 47/48338; A61K 47/48715; A61K 47/48761; A61K 47/48407
See application file for complete search history.

(56) References Cited

U.S. PATENT DOCUMENTS

| | | | | |
|---|---|---|---|---|
| 6,214,345 | B1* | 4/2001 | Firestone | A61K 47/48369 424/178.1 |
| 7,387,771 | B1 | 6/2008 | Kratz | |
| 8,642,555 | B2 | 2/2014 | Kratz et al. | |
| 9,408,910 | B2* | 8/2016 | Ryu | A61K 47/48246 |
| 9,408,911 | B2* | 8/2016 | Ryu | A61K 47/48246 |
| 2013/0338422 | A1* | 12/2013 | Ryu | A61K 47/48246 600/1 |

FOREIGN PATENT DOCUMENTS

WO     WO 2012/118237 A1 *  7/2012

OTHER PUBLICATIONS

Di ("Strategic Approaches to Optimizing Peptide ADME Properties," AAPS Journal, 2015, vol. 17, pp. 134-141).*
Schmid et al. "Albumin-Binding Prodrugs of Camptothecin and Doxorubicin with an Ala-Leu-Ala-Leu-Linker That Are Cleaved by Cathepsin B: Synthesis and Antitumor Efficacy," Bioconjugate Chem. 2007, 18, 702-716.*
Kopeček et al., "HPMA copolymer-anticancer drug conjugates: design, activity, and mechanism of action," European Journal of Pharmacetuics and Biopharmaceutics, vol. 50, pp. 61-81, Jul. 2000.
Kim et al., "Current advances in mathematical modeling of anticancer drug penetration into tumor tissues," Frontiers in Oncology, vol. 3, Article 278, pp. 1-10, Nov. 2013.
Chauhan et al., "Delivery of Molecular and Nanoscale Medicine to Tumors: Transport Barriers and Strategies," Annu. Rev. Chem. Biomol. Eng., vol. 2, pp. 281-298, Mar. 2011.
Khawar et al., "Improving drug delivery to solid tumors: Priming the tumor microenvironment," Journal of Controlled Release, vol. 201, pp. 78-89, Dec. 2014.
Xie et al., "An Albumin-Conjugated Peptide Exhibits Potent Anti-HIV Activity and Long In Vivo Half-Life," Antimicrobial Agents and Chemotherapy, vol. 54, No. 1, pp. 191-196, Jan. 2010.
Zhao et al., "A rapid albumin-binding 5-fluorouracil prodrug with a prolonged circulation time and enhanced antitumor activity," Biomaterials Science, vol. 5, pp. 502-510, Jan. 2017.
Lee et al., "Induced Phenotype Targeted Therapy: Radiation-Induced Apoptosis-Targeted Chemotherapy," JNCI J Natl Cancer Inst., pp. 1-9, Dec. 2014.
Flanagan et al., "Evaluation of protein-N-(2-hydroxypropyl) methacrylamide copolymer conjugates as targetable drug carriers. 1. Binding, pinocytic uptake and intracellular distribution of transferrin and anti-transferrin receptor antibody conjugates," Biochimca et Biophysica Acta, vol. 993, pp. 83-91, Oct. 1989.

* cited by examiner

*Primary Examiner* — Christina Bradley
(74) *Attorney, Agent, or Firm* — Foley & Lardner LLP

(57) ABSTRACT

Described are prodrug conjugates that release a chemotherapeutic agent upon activation by caspase, and methods using such prodrug conjugates to induce apoptosis, amplify apoptosis, and treat cancer.

50 Claims, 15 Drawing Sheets

SEQUENCE LISTING

<160> NUMBER OF SEQ ID NOS: 43

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 1

Asp Xaa Xaa Asp
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 2

Leu Xaa Xaa Asp
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 3

Val Xaa Xaa Asp
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Glu Val Asp
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 5

Asp Leu Val Asp
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Glu Ile Asp
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Glu His Asp
1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Gly Asp Glu Val Asp
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Gln Arg Pro Pro Arg
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term maleimide
<220> FEATURE:
<223> OTHER INFORMATION: C-term PABC-doxorubicin

<400> SEQUENCE: 10

Lys Gly Asp Glu Val Asp
1               5
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term maleimide
<220> FEATURE:
<223> OTHER INFORMATION: C-term PABC-daunorubicin

<400> SEQUENCE: 11

Lys Gly Asp Glu Val Asp
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term maleimide
<220> FEATURE:
<223> OTHER INFORMATION: C-term PABC-paclitaxel

<400> SEQUENCE: 12

Lys Gly Asp Glu Val Asp
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term maleimide
<220> FEATURE:
<223> OTHER INFORMATION: C-term PABC-MMAE

<400> SEQUENCE: 13

Lys Gly Asp Glu Val Asp
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term maleimide
<220> FEATURE:
<223> OTHER INFORMATION: C-term PABC-doxorubicin

<400> SEQUENCE: 14

Asp Glu Val Asp
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: N-term maleimide
<220> FEATURE:
<223> OTHER INFORMATION: C-term PABC-doxorubicin

<400> SEQUENCE: 15

Asp Glu Ile Asp
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term maleimide
<220> FEATURE:
<223> OTHER INFORMATION: C-term PABC-doxorubicin

<400> SEQUENCE: 16

Asp Leu Val Asp
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term maleimide
<220> FEATURE:
<223> OTHER INFORMATION: C-term doxorubicin

<400> SEQUENCE: 17

Asp Glu Val Asp
1

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term pyridyldithiol
<220> FEATURE:
<223> OTHER INFORMATION: C-term PABC-doxorubicin

<400> SEQUENCE: 18

Lys Gly Asp Glu Val Asp
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term oleate
<220> FEATURE:
<223> OTHER INFORMATION: C-term PABC-doxorubicin
```

```
<400> SEQUENCE: 19

Lys Gly Asp Glu Val Asp
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term polyethylene glycol
<220> FEATURE:
<223> OTHER INFORMATION: C-term PABC-doxorubicin

<400> SEQUENCE: 20

Lys Gly Asp Glu Val Asp
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term hyaluronan
<220> FEATURE:
<223> OTHER INFORMATION: C-term PABC-doxorubicin

<400> SEQUENCE: 21

Lys Gly Asp Glu Val Asp
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term folate
<220> FEATURE:
<223> OTHER INFORMATION: C-term PABC-doxorubicin

<400> SEQUENCE: 22

Lys Gly Asp Glu Val Asp
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term PABC-doxorubicin

<400> SEQUENCE: 23

Arg Gly Asp Glu Val Asp
1               5
```

```
<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term PABC-doxorubicin

<400> SEQUENCE: 24

Cys Gln Arg Pro Pro Arg Asp Glu Val Asp
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term MBA-doxorubicin

<400> SEQUENCE: 25

Arg Gly Asp Glu Val Asp
1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term daunorubicin

<400> SEQUENCE: 26

Asp Glu Val Asp
1

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term daunorubicin

<400> SEQUENCE: 27

Arg Gly Asp Ser Cys
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term HSA-maleimide
<220> FEATURE:
<223> OTHER INFORMATION: C-term PABC-doxorubicin
```

```
<400> SEQUENCE: 28

Lys Gly Asp Glu Val Asp
1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term maleimide
<220> FEATURE:
<223> OTHER INFORMATION: C-term MMAE

<400> SEQUENCE: 29

Asp Glu Val Asp
1

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic
<220> FEATURE:
<223> OTHER INFORMATION: C-term PABC-doxorubicin

<400> SEQUENCE: 30

Cys Arg Gly Asp Cys Gly Gly Asp Glu Val Asp
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term HSA
<220> FEATURE:
<223> OTHER INFORMATION: C-term PABC-doxorubicin

<400> SEQUENCE: 31

Lys Gly Asp Glu Val Asp
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term PABC-doxorubicin

<400> SEQUENCE: 32

Lys Gly Asp Glu Val Asp
1               5
```

```
<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac

<400> SEQUENCE: 33

Lys Gly Asp Glu Val Asp
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys(OAloc)
<220> FEATURE:
<221> NAME/KEY: MOD_RES
<222> LOCATION: (3)..(3)
<223> OTHER INFORMATION: Asp(OAll)
<220> FEATURE:
<221> NAME/KEY: MOD_RES
<222> LOCATION: (4)..(4)
<223> OTHER INFORMATION: Glu(OAll)
<220> FEATURE:
<221> NAME/KEY: MOD_RES
<222> LOCATION: (6)..(6)
<223> OTHER INFORMATION: Asp(OAll)
<220> FEATURE:
<223> OTHER INFORMATION: C-term OH

<400> SEQUENCE: 34

Lys Gly Asp Glu Val Asp
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Gly Asp Ser Cys
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys(OAloc)
```

```
<220> FEATURE:
<221> NAME/KEY: MOD_RES
<222> LOCATION: (3)..(3)
<223> OTHER INFORMATION: Asp(OAll)
<220> FEATURE:
<221> NAME/KEY: MOD_RES
<222> LOCATION: (4)..(4)
<223> OTHER INFORMATION: Glu(OAll)
<220> FEATURE:
<221> NAME/KEY: MOD_RES
<222> LOCATION: (6)..(6)
<223> OTHER INFORMATION: Asp(OAll)
<220> FEATURE:
<223> OTHER INFORMATION: C-term PABOH

<400> SEQUENCE: 36

Lys Gly Asp Glu Val Asp
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys(OAloc)
<220> FEATURE:
<221> NAME/KEY: MOD_RES
<222> LOCATION: (3)..(3)
<223> OTHER INFORMATION: Asp(OAll)
<220> FEATURE:
<221> NAME/KEY: MOD_RES
<222> LOCATION: (4)..(4)
<223> OTHER INFORMATION: Glu(OAll)
<220> FEATURE:
<221> NAME/KEY: MOD_RES
<222> LOCATION: (6)..(6)
<223> OTHER INFORMATION: Asp(OAll)
<220> FEATURE:
<223> OTHER INFORMATION: C-term PABC

<400> SEQUENCE: 37

Lys Gly Asp Glu Val Asp
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys(OAloc)
<220> FEATURE:
<221> NAME/KEY: MOD_RES
<222> LOCATION: (3)..(3)
<223> OTHER INFORMATION: Asp(OAll)
<220> FEATURE:
<221> NAME/KEY: MOD_RES
<222> LOCATION: (4)..(4)
<223> OTHER INFORMATION: Glu(OAll)
```

```
<220> FEATURE:
<221> NAME/KEY: MOD_RES
<222> LOCATION: (6)..(6)
<223> OTHER INFORMATION: Asp(OAll)
<220> FEATURE:
<223> OTHER INFORMATION: C-term PABC-doxorubicin

<400> SEQUENCE: 38

Lys Gly Asp Glu Val Asp
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys(EMC)
<220> FEATURE:
<223> OTHER INFORMATION: C-term PABC-doxorubicin

<400> SEQUENCE: 39

Lys Gly Asp Glu Val Asp
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Gly Asp Glu Val Asp
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Gln Arg Pro Pro Arg Asp Glu Val Asp
1               5                   10

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term MBA-doxorubicin

<400> SEQUENCE: 42

Arg Gly Asp Glu Val Asp
1               5
```

```
<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 43

Arg Gly Asp Glu Val Asp Cys
1               5
```

PRODRUGS ACTIVATED BY CASPASE

CROSS-REFERENCE TO RELATED APPLICATIONS

This application claims the priority benefits of U.S. provisional patent application 62/114,126, filed Feb. 10, 2015 and Korean application 10-2014-0162555 filed Nov. 20, 2014, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Oct. 22, 2015, is named 109707-0104SL.txt and is 12,100 bytes in size.

FIELD OF INVENTION

Described are prodrug conjugates capable of releasing a drug upon activation by caspase, related methods of inducing apoptosis, amplifying apoptosis, and treating cancer.

BACKGROUND

Chemotherapy is the most frequently applied anticancer therapy because of its powerful anticancer effect. Nevertheless the use of chemotherapy often is restricted because of serious side effects and toxicity. Efforts to develop selective chemotherapy that targets tumors as opposed to healthy tissue have focused on targeted delivery of chemotherapeutic agents to tumor cells, such as by using antibodies or peptides that recognize and bind to molecules expressed preferentially in tumor cells but not normal cells. However, wide use of such drugs is limited since such drugs can only be administered to patients whose tumor cells express the target molecules. Moreover, recent research has shown that even within a given patient tumor cells may exhibit intratumoral heterogeneity, with genetic phenotypes differing among cancer cells within a single tumor tissue. This means that even if a biopsy confirms the expression of the target molecule for a given drug, all tumor cells may not express the target, thereby limiting the therapeutic effectiveness of the drug. Furthermore, even when the majority of the tumor tissue expresses the target molecule, the drug still may affect other cells with which it comes into proximity or contact, causing side effects or toxicity.

In further efforts to address these problems, prodrugs have been developed that may be specifically activated in tumor cells and tumor tissue. For example, U.S. Pat. No. 7,445,764 describes a conjugate of a cleavable matrix metalloproteinase (MMP) cleavable peptide and the anticancer drug doxorubicin. US Pat. App. Pub. 2010/0111866 discloses a possible variation of that prodrug conjugated to maleimide. US Pat. App. Pub. 2010/0111866 discloses a prodrug conjugate in the form of maleimide-hydrazone-doxorubicin. US Pat. App. Pub. 2013/0338422 describes a prodrug conjugate of a peptide sequence—DEVD (SEQ ID NO: 4)—and doxorubicin. However, these conjugates suffer from one or more of poor efficacy and poor selectivity, and/or require frequent dosing.

Thus, there remains a need for chemotherapy that works selectively in tumor cells and does not harm normal tissue, such as prodrugs that exhibit good efficacy with minimal side effects.

SUMMARY

In some embodiments, there are provided prodrug conjugates comprising: (i) a functional moiety, (ii) a caspase-cleavable peptide linker, and (iii) a chemotherapeutic agent, wherein the functional moiety exhibits one or more functions selected from the group consisting of localizing at a target cell, binding to a target cell, accumulating in tumor tissues, and prolonging plasma circulation of the conjugate. In some embodiments, there are provided methods of inducing apoptosis and/or methods of amplifying apoptosis using the conjugates described herein. In some embodiments, there are provided methods of treating cancer using the conjugates described herein.

In specific embodiments, there are provided chemotherapeutic prodrug conjugates comprising: (i) a functional moiety, joined directly or through a linker to (ii) a caspase-cleavable peptide linker, joined directly or through a linker to (iii) a chemotherapeutic agent, wherein the functional moiety exhibits one or more functions selected from the group consisting of localizing at a target cell, binding to a target cell, accumulating in tumor tissues, and prolonging plasma circulation of the conjugate.

In certain embodiments, the functional moiety is selected from the group consisting of maleimide, N-hydroxysuccinimide ester, halogenacetamide, halogenacetate, aziridine, disulfide, acetylene, pyridylthio, vinylcarbonyl, albumin, transferrin, polyethylene glycol, and hyaluronic acid. In other embodiments, the functional moiety is selected from the group consisting of antibodies, proteins, aptamers, oligonucleotides and saccharides that bind selectively to tumor cells or tumor endothelial cells. In still other embodiments, the functional moiety is selected from the group consisting of RGD, cyclic-RGD, folic acid, and peptides comprising the amino acid sequence Cys-Gln-Arg-Pro-Pro-Arg (SEQ ID NO:9). In a specific embodiment, the functional moiety is maleimide.

In certain embodiments, the caspase-cleavable peptide linker is cleavable by a caspase selected from the group consisting of caspase-3, caspase-7, and caspase-9. In certain embodiments, the four C-terminal amino acid residues of the caspase-cleavable peptide linker are selected from the group consisting of Asp-Xaa-Xaa-Asp (SEQ ID NO:1), Leu-Xaa-Xaa-Asp (SEQ ID NO:2), and Val-Xaa-Xaa-Asp (SEQ ID NO:3), where Xaa represents any amino acid residue. In further embodiments, the four C-terminal amino acid residues of the caspase-cleavable peptide linker are selected from the group consisting of Asp-Glu-Val-Asp (SEQ ID NO:4), Asp-Leu-Val-Asp (SEQ ID NO:5) Asp-Glu-Ile-Asp (SEQ ID NO:6), and Leu-Glu-His-Asp (SEQ ID NO:7). In a specific embodiment, the six C-terminal amino acid residues of the caspase-cleavable peptide linker consist of Lys-Gly-Asp-Glu-Val-Asp (SEQ ID NO:8).

In certain embodiments, the chemotherapeutic agent induces apoptosis of tumor cells. In some embodiments, chemotherapeutic agent is selected from the group consisting of anthracyclines, antibiotics, alkylating agents, platinum-based agents, antimetabolites, topoisomerase inhibitors, and mitotic inhibitors. In some embodiments, the chemotherapeutic agent is selected from the group consisting of doxorubicin, daunorubicin, epirubicin, idarubicin, valrubicin, and derivatives thereof. In other embodiments, the chemotherapeutic agent is selected from the group consisting of actinomycin-D, bleomycin, mitomycin-C, calicheamicin, and derivatives thereof. In still other embodiments, the chemotherapeutic agent is selected from the group consisting of cyclophosphamide, mechlorethamine, uramustine, melphalan, chlorambucil, ifosfamide, bendamustine, carmustine, lomustine, streptozocin, busulfan, dacarbazine, temozolomide, thiotepa, altretamine, duocarmycin, cisplatin, carboplatin, nedaplatin, oxaliplatin, satraplatin, triplatin tetranitrate, 5-fluorouracil, 6-mercaptopurine, capecitabine, cladribine, clofarabine, cystarbine, floxuridine, fludarabine, gemcitabine, hydroxyurea, methotrexate, pemetrexed, pentostatin, thioguanine, camptothecin, topotecan, irinotecan, etoposide, teniposide, mitoxantrone, paclitaxel, docetaxel, izabepilone, vinblastine, vincristine, vindesine, vinorelbine, estramustine, maytansine, DM1 (mertansine), DM4, dolastatin, auristatin E, auristatin F, monomethyl auristatin E, monomethyl auristatin F, and derivatives thereof.

In a specific embodiment, the functional moiety is maleimide, the caspase-cleavable peptide linker has an amino acid sequence consisting of Lys-Gly-Asp-Glu-Val-Asp (SEQ ID NO:8), and the chemotherapeutic agent is doxorubicin.

In certain embodiments, the conjugate is selected from the group consisting Maleimide-KGDEVD-PABC-Doxorubicin (SEQ ID NO: 10), Maleimide-KGDEVD-PABC-Daunorubicin (SEQ ID NO: 11), Maleimide-KGDEVD-PABC-Paclitaxel (SEQ ID NO: 12), Maleimide-KGDEVD-PABC-MMAE (SEQ ID NO: 13), Maleimide-DEVD-PABC-Doxorubicin (SEQ ID NO: 14), Maleimide-DEID-PABC-Doxorubicin (SEQ ID NO: 15), Maleimide-DLVD-PABC-Doxorubicin (SEQ ID NO: 16), Maleimide-DEVD-Doxorubicin (SEQ ID NO: 17), Pyridyldithiol-KGDEVD-PABC-Doxorubicin (SEQ ID NO: 18), Oleate-KGDEVD-PABC-Doxorubicin (SEQ ID NO: 19), Polyethylene glycol-KGDEVD-PABC-Doxorubicin (SEQ ID NO: 20), Hyaluronan-KGDEVD-PABC-Doxorubicin (SEQ ID NO: 21), Folate-KGDEVD-PABC-Doxorubicin (SEQ ID NO: 22), RGDEVD-PABC-Doxorubicin (SEQ ID NO: 23), CQRPPRDEVD-PARC-Doxorubicin (SEQ ID NO: 24), RGDEVD-MBA-Doxorubicin (SEQ ID NO: 25), DEVD-Daunorubicin-RGDSC (SEQ ID NOS 26 and 27), and HSA-Maleimide-KGDEVD-PABC-Doxorubicin (SEQ ID NO: 28).

In specific embodiments, there are provided chemotherapeutic prodrug conjugates comprising: (i) a caspase-cleavable peptide, joined directly or through a linker to (ii) daunorubicin, joined directly or through a linker at its 14-$CH_3$ to (iii) a functional moiety, wherein the functional moiety exhibits one or more functions selected from the group consisting of localizing at a target cell, binding to a target cell, accumulating in tumor tissues, and prolonging plasma circulation of the conjugate.

In some embodiments, there are provided compositions comprising a prodrug conjugate, as described above, and a pharmaceutically acceptable carrier. In further embodiments, the composition is formulated for intravenous administration.

In specific embodiments, there are provided methods of amplifying apoptosis in tumor cells in a subject comprising inducing apoptosis in tumor cells thereby inducing expression of caspase, and administering to the subject a prodrug conjugate as described herein.

In specific embodiments, there are provided methods of treating cancer in a subject in need thereof comprising treating the subject with an apoptosis inducing treatment effective to induce expression of caspase and administering to the subject a conjugate according to any one of the preceding claims. In some embodiments, apoptosis is induced before the conjugate is administered. In some embodiments, apoptosis also is induced after the conjugate is administered.

In specific embodiments, there are provided methods of amplifying apoptosis in tumor cells in a subject, comprising administering a conjugate as described herein to a subject in need thereof who has been treated with a first apoptosis inducing treatment effective to induce expression of caspase. In some embodiments, the methods further include treating the subject with a second apoptosis inducing treatment effective to induce expression of caspase.

In any embodiments with a first and second apoptosis inducing treatment, the second apoptosis inducing treatment may be the same as or different from the first apoptosis inducing treatment.

In certain embodiments, the apoptosis is induced by a treatment selected from the group consisting of radiation, hyperthermia, laser therapy, photodynamic therapy, chemotherapy, and cryosurgery. In further embodiments, the apoptosis is induced by treatment by a targeted therapy using an agent that targets tumor cells. In other embodiments, the apoptosis is induced by treatment with a chemotherapeutic agent selected from the group consisting anthracyclines, antibiotics, alkylating agents, platinum-based agents, antimetabolites, topoisomerase inhibitors, and mitotic inhibitors.

In a specific embodiment the apoptosis is induced by radiation therapy. In further embodiments, the radiation therapy is selected from the group consisting of gamma-knife radiation, cyber-knife radiation, and high intensity focused ultrasound radiation. In some embodiments, the radiation is applied at a dose of up to about 70 Gy. In some embodiments, the radiation is applied as a single dose of up to about 35 Gy or at weekly doses of up to about 10 Gy.

In certain embodiments, the conjugate is administered intravenously.

The foregoing summary is illustrative only and is not intended to be in any way limiting. In addition to the illustrative aspects, embodiments, and features described above, further aspects, embodiments, and features will become apparent by reference to the detailed description and examples herein below.

DETAILED DESCRIPTION

Figure 1:
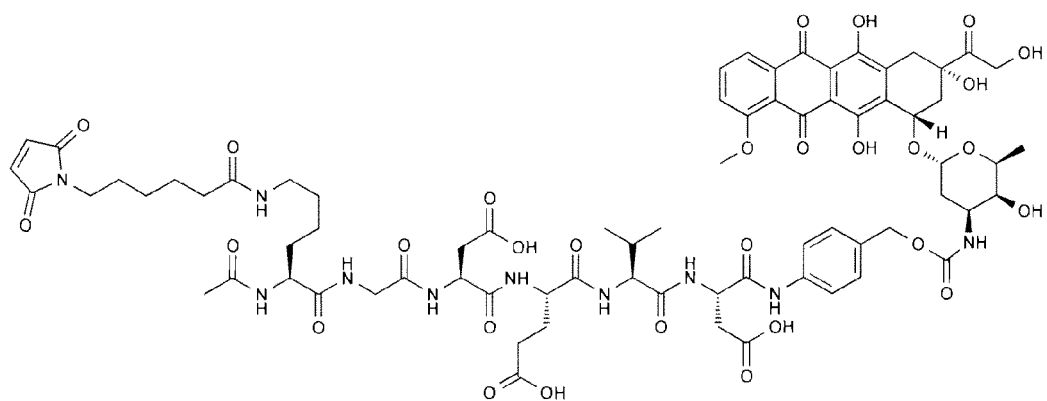
FIG. 1 depicts the chemical structure of maleimide-KGDEVD-PABC-doxorubicin (SEQ ID NO: 10).

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any made are incorporated herein by reference in their entireties as though set forth in full. Any suitable materials and/or methods known to those of ordinary skill in the art can be utilized in carrying out the present invention. However, specific materials and methods are described for illustrative purposes. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" means that the number comprehended is not limited to the exact number set forth herein, and is intended to refer to ranges substantially around the number without departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular number.

As used herein, the term "tumor cell(s)" refers to the cells of any type of tumor tissue, benign or malignant.

As used herein, the term "cancer" refers to cancer originating from any part of the body or any cell type. This includes, but is not limited to, carcinoma, sarcoma, lymphoma, germ cell tumors, and blastoma. In some embodiments, the cancer is associated with a specific location in the body or a specific disease.

As used herein, the term "subject" refers to any animal in need of treatment by any one or more of the methods described herein, including humans and other mammals, such as dogs, cats, rabbit, horses, and cows. For example, a subject may be suffering from or at risk of developing a condition that can be treated or prevented with an apoptosis inducing treatment. In specific embodiments, the subject is a human with a tumor. In further specific embodiments, the tumor is malignant. In further specific embodiments, the subject is a human diagnosed with cancer.

Prodrug Conjugates

Described herein are prodrug conjugates comprising: (i) a functional moiety, (ii) a caspase-cleavable peptide linker, and (iii) a chemotherapeutic agent, wherein the functional moiety exhibits one or more functions selected from the group consisting of localizing at a target cell, binding to a target cell, accumulating in tumor tissues, and prolonging plasma circulation of the conjugate. As discussed in more detail below, the conjugates are useful, for example, in methods of inducing apoptosis, methods of amplifying apoptosis, and methods of treating cancer.

Functional Moiety

As noted above, the prodrug conjugates described herein include a functional moiety. As used herein, the term "functional moiety" refers to any moiety that exhibits one or more functions selected from the group consisting of localizing at a target cell, binding to a target cell, accumulating in tumor tissues, and prolonging plasma circulation of the conjugate. In some embodiments related to targeting, the functional moiety binds selectively with molecules expressed by or near target cells. In some embodiments related to prolonging plasma circulation, the functional moiety binds to circulating plasma proteins. In any embodiments, the functional moiety may comprise one or more of functional chemical groups, peptide moieties, antibody moieties (including antibody fragments and single-chain antibody moieties), aptamers, oligonucleotides or saccharides. In some embodiments, the functional moiety may be a polymer.

In some embodiments, the functional moiety passively targets the conjugate to tumor tissue via the Enhanced Permeability and Retention (EPR) effect.

In specific embodiments, the functional moiety is selected from one or more of proteins such as albumin and transferrin; polymers such as polyethylene glycol, hyaluronic acid; functional groups that bind with albumin such as maleimide groups, halogenacetamide, halogenacetate, pyridylthio, vinylcarbonyl, aziridine, disulfide, acetylene, and N-hydroxysuccinimide ester. In other embodiments, the functional moiety is selected from one or more of the peptide Arg-Gly-Asp ("RGD"), cyclic-RGD, peptides containing one or more RGD sequences, and folic acid. In specific embodiments, the functional moiety is maleimide.

In some embodiments, the functional moiety has a strong affinity to an endogenous substance or substances, such as proteins found selectively in target tissue or target cells, e.g., tumor tissue or tumor cells. In accordance with these embodiments, the functional moiety may be selected from one or more of RGD (which selectively binds with integrin $\alpha_v\beta_3$) or peptides that contain ROD sequence; the peptide sequence Cys-Gln-Arg-Pro-Pro-Arg (SEQ ID NO: 9) (which selectively binds with histone H1, which is released from the nuclei of tumor cells undergoing apoptosis), peptides comprising SEQ ID NO: 9 or a similar sequence exhibiting a similar function, and folic acids (which bind with folic acid receptors).

Caspase Cleavable Peptide Linker

As noted above, the prodrug conjugates described herein include a caspase-cleavable peptide linker.

As used herein, the term "caspase" refers to cysteine-aspartic proteases and cysteine-dependent aspartate-directed proteases that are activated (e.g., expressed) by cells undergoing apoptosis. In specific embodiments, the caspase is caspase-3, caspase-7, and/or caspase-9.

As used herein, the term "amino acid" refers to any amino acid, including naturally-occurring amino acids and non-naturally-occurring amino acids, including synthetically made naturally-occurring amino acids. The natural amino acids, with exception of glycine, contain a chiral carbon atom. Thus, amino acids can be in the form of an L or D isomer. Specific examples of amino acids include (3-alanine (BALA), γ-aminobutyric acid (GABA), 5-aminovaleric acid, glycine (Gly or G), phenylglycine, arginine (Arg or R), homoarginine (Har or hR), alanine (Ala or A), valine (Val or V), norvaline, leucine (Leu or L), norleucine (Nle), isoleucine (Ile or I), serine (Ser or 5), isoserine, homoserine (Hse), threonine (Thr or T), allothreonine, methionine (Met or M), ethionine, glutamic acid (Glu or E), aspartic acid (Asp or D), asparagine (Asn or N), cysteine (Cys or C), cystine, phenylalanine, tyrosine (Tyr or Y), tryptophan (Trp or W), lysine (Lys or K), hydroxylysine (Hyl), histidine (His or H), ornithine (Orn), glutamine (Gln or Q), citrulline, proline (Pro or P), and 4-hydroxyproline (Hyp or O).

As used herein, the term "peptide" refers to peptides and peptide analogs, wherein peptide analogs may include naturally-occurring amino acids and non-naturally-occurring amino acids, modifications such as glycosylations, modified R groups, and/or modified peptide backbones. In some embodiments, a peptide comprises only L-isomers of its chiral amino acids. In other embodiments, a peptide comprises only D-isomers of its chiral amino acids. In other embodiments, a peptide comprises both L-isomers and D-isomers of one or more of its chiral amino acids. The term "peptide" also includes peptides or peptide analogs that include amino acid mimetics that function in a manner similar to the naturally-occurring amino acids. In specific embodiments, peptide analogs include at least one bond in the peptide sequence which is different from an amide bond, such as urethane, urea, ester or thioester bond. Peptides or peptide analogs as used herein can be linear, cyclic or branched, but typically are linear.

As used herein, the term "caspase-cleavable peptide linker" refers to a peptide sequence of two or more one amino acid residues that is capable of being cleaved by caspase. In some embodiments, the caspase cleavable peptide linker is cleavable by caspase-3 or caspase-7, such as peptides comprising the sequence Asp-Xaa-Xaa-Asp (SEQ ID NO:1) (where "Xaa" represents any amino acid, in L- or D-isomer form). In some embodiments, the caspase-cleavable peptide linker is cleavable by caspase-9, such as peptides comprising the amino acid sequence Leu-Xaa-Xaa-Asp (SEQ ID NO:2) or Val-Xaa-Xaa-Asp (SEQ ID NO:3) (where "Xaa" represents any amino acid, in L- or D-isomer form).

In specific embodiments, the caspase-cleavable peptide linker comprises one of the following sequences:

```
                                        (SEQ ID NO: 4)
            Asp-Glu-Val-Asp (SEQ ID NO: 5)
            Asp-Leu-Val-Asp (SEQ ID NO: 6)
            Asp-Glu-Ile-Asp,
            or (SEQ ID NO: 7)
            Leu-Glu-His-Asp.
```

In specific embodiments, the caspase-cleavable peptide linker comprises the sequence Lys-Gly-Asp-Glu-Val-Asp (SEQ ID NO:8), also denoted as KGDEVD (SEQ ID NO 8).

In certain embodiments, the presence of the caspase-cleavable linker renders the prodrug conjugate inactive until the linker is cleaved. In accordance with such embodiments, the prodrug conjugate exerts minimal damage to healthy cells, because it only is activated in the presence of caspase, e.g., in the presence of cells undergoing apoptosis, such as tumor cells undergoing apoptosis. Thus, in certain embodiments, the prodrug conjugates described herein exhibit minimal side effects.

Chemotherapeutic Agent

As noted above, the prodrug conjugates described herein include a chemotherapeutic agent.

As used herein, the term "chemotherapeutic agent" refers to a moiety useful to treat cancer, such as a small molecule chemical compound used to treat cancer. In specific embodiments, the chemotherapeutic agent induces apoptosis in target cells, e.g., in tumor cells and tumor tissue. Any chemotherapeutic agent known in the art can be used as a chemotherapeutic agent in the conjugates described herein.

In some embodiments, the chemotherapeutic agent is an anthracycline, such as doxorubicin, daunorubicin, epirubicin, idarubicin, valrubicin, or a derivative thereof; an antibiotic, such as actinomycin-D, bleomycin, mitomycin-C, calicheamicin, or a derivative thereof; an alkylating agent, such as cyclophosphamide, mechlorethamine, uramustine, melphalan, chlorambucil, ifosfamide, bendamustine, carmustine, lomustine, streptozocin, busulfan, dacarbazine, temozolomide, thiotepa, altretamine, duocarmycin, or a derivative thereof; a platinum-based agent, such as cisplatin, carboplatin, nedaplatin, oxaliplatin, satraplatin, triplatin tetranitrate, or a derivative thereof; an antimetabolite, such as 5-fluorouracil, 6-mercaptopurine, capecitabine, cladribine, clofarabine, cystarbine, floxuridine, fludarabine, gemcitabine, hydroxyurea, methotrexate, pemetrexed, pentostatin, thioguanine, or a derivative thereof; a topoisomerase inhibitor, such as camptothecin, topotecan, irinotecan, etoposide, teniposide, mitoxantrone, or a derivative thereof; a mitotic inhibitor, such as paclitaxel, docetaxel, izabepilone, vinblastine, vincristine, vindesine, vinorelbine, estramustine, maytansine, DM1 (mertansine), DM4, dolastatin, auristatin E, auristatin F, monomethyl auristatin E, monomethyl auristatin F, or a derivative thereof. In specific embodiments, the chemotherapeutic agent is doxorubicin or danorubicin.

Linkages and Linkers Conjugates

In some embodiments of the prodrug conjugates described herein, the functional moiety may be joined directly or through a linker to the caspase-cleavable peptide linker, and the caspase-cleavable peptide linker may be joined directly or through a linker to the chemotherapeutic agent. Thus, in certain embodiments the functional moiety is conjugated directly to the caspase-cleavable peptide linker, such as by a covalent bond between a moiety on the functional moiety and a moiety at the N-terminus of the peptide linker or on a side chain of the peptide linker. Independently, in some embodiments the caspase-cleavable peptide linker is conjugated directly to the chemotherapeutic agent, such as by a covalent bond between a moiety at the C-terminus of the peptide linker or on a side chain of the peptide linker and a moiety on the chemotherapeutic agent.

Alternatively, one or both of the linkages may be through a linker. Any linker suitable for use in pharmaceutical compounds may be used for this purpose. Suitable linkers are illustrated in the examples, including PABC.

Although the above description assumes that the functional moiety is linked to the N-terminus of the caspase-cleavable peptide linker, while the chemotherapeutic agent is linked to the C-terminus of the caspase-cleavable peptide linker, also contemplated are prodrug conjugates wherein the chemotherapeutic agent is linked to the N-terminus of the caspase-cleavable peptide linker, while the functional moiety is linked to the C-terminus of the caspase-cleavable peptide linker.

In still other embodiments, a prodrug conjugate as described herein includes a caspase-cleavable peptide joined directly or through a linker to a chemotherapeutic agent, which is joined directly or through a linker to a functional moiety. For example, daunorubicin exhibits its chemotherapeutic effect when it is conjugated at its 14-$CH_3$ position to a functional moiety, such as linear or cyclic RGD or folate. Thus, caspase-induced cleavage need not release free daunorubicin in order to provide a chemotherapeutic effect. Thus, in some embodiments a prodrug conjugate comprises a caspase-cleavable peptide joined directly or through a linker to daunorubicin, which is joined at its 14-$CH_3$ position directly or through a linker to a functional moiety, such as linear or cyclic RGD or folate. One example of these embodiments is illustrated in Example 16 below.

Specific examples of prodrug conjugates are set forth in the examples below and in the figures, including Maleimide-KGDEVD-PABC-Doxorubicin (SEQ ID NO: 10), Maleimide-KGDEVD-PABC-Daunorubicin (SEQ ID NO: 11), Maleimide-KGDEVD-PABC-Paclitaxel (SEQ ID NO: 12), Maleimide-KGDEVD-PABC-MMAE (SEQ ID NO: 13), Maleimide-DEVD-PABC-Doxorubicin (SEQ ID NO: 14), Maleimide-DEID-PABC-Doxorubicin (SEQ ID NO: 15), Maleimide-DLVD-PABC-Doxorubicin (SEQ ID NO: 16), Maleimide-DEVD-Doxorubicin (SEQ ID NO: 17), Maleimide-DEVD-MMAE (SEQ ID NO: 29), Pyridyldithiol-KGDEVD-PABC-Doxorubicin (SEQ ID NO: 18), Oleate-KGDEVD-PABC-Doxorubicin (SEQ ID NO: 19), Polyethylene glycol-KGDEVD-PABC-Doxorubicin (SEQ ID NO: 20), Hyaluronan-KGDEVD-PABC-Doxorubicin (SEQ ID NO: 21), Folate-KGDEVD-PABC-Doxorubicin (SEQ ID NO: 22), RGDEVD-PABC-Doxorubicin (SEQ ID NO: 23), CQRPPRDEVD-PABC-Doxorubicin (SEQ ID NO: 24), RGDEVD-MBA-Doxorubicin (SEQ ID NO: 25), DEVD-Daunorubicin-RGDSC (SEQ ID NOS 26 and 27), HSA-Maleimide-KGDEVD-PABC-Doxorubicin (SEQ ID NO: 28).

In some embodiments, the prodrug conjugate is provided in a pharmaceutical composition, such as a composition comprising the prodrug conjugate and a pharmaceutically acceptable carrier, excipient, and/or diluent. Examples of suitable carriers, excipients, and diluents include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, minerals, and the like.

The pharmaceutical composition may be prepared for any route of administration, including any parenteral or local route of administration. In some embodiments, the pharmaceutical composition is suitable for injection or infusion, such as for intravenous injection or infusion, such as being prepared as a sterile composition for injection or infusion. In other embodiments, the pharmaceutical composition is suitable for oral administration, such as being prepared in a powder, granule, tablet, capsule, suspension, emulsion, or syrup form. In other embodiments, the pharmaceutical composition is suitable for inhalation, such as being in the form of a nasal or oral spray or aerosol. In other embodiments, the pharmaceutical composition is suitable for rectal or vaginal administration, such as being in a suppository formulation. In other embodiments, the pharmaceutical composition is suitable for topical or transdermal administration, such as being in a solution, emulsion, gel, or patch. Appropriate components and excipients for such compositions are known in the art.

Examples of a solid formulation for oral administration include a tablet, a pill, a powder, a granule, a capsule or the like. Solid formulations can be manufactured by mixing the conjugate with at least one excipient, for example, starch, calcium carbonate, sucrose, lactose, gelatin or the like. In addition to the simple excipient, a lubricant such as magnesium stearate or talc may be used to aid tableting or other processing.

Examples of liquid formulation for oral administration include solutions, suspensions, emulsions and syrups. A liquid formulation may include various excipients, for example, a wetting agent, a sweetener, an aromatic, a preservative, or the like, in addition to water and, optionally, liquid paraffin.

Examples of other formulations for parenteral administration include sterilized aqueous solutions, water-insoluble solutions, suspensions, emulsions, lyophilized formulations, and suppositories. Non-aqueous solutions and suspensions may include, for example, propylene glycol, polyethylene glycol, a plant oil such as olive oil, or injectable ester such as ethyloleate. A base for a suppository formulation may include, for example, witepsol, macrogol, Tween 61, cacao butter, laurin butter, glycerogelatin or the like.

In specific embodiments, the conjugate is dissolved in water or another pharmaceutically acceptable aqueous carrier in which the conjugate exhibits good solubility, optionally with or without other pharmaceutical acceptable excipients, preservatives, and the like.

Methods Using Prodrug Conjugates

As noted above, the prodrug conjugates described herein are useful in methods of inducing apoptosis, methods of amplifying apoptosis, and methods of treating cancer. In some embodiments, the prodrug conjugate is administered to a subject in need of inducing apoptosis of target cells (e.g., tumor cells), of amplifying apoptosis of target cells, and/or in need of treatment of cancer.

In some embodiments, the subject is subjected to a treatment that induces apoptosis in target cells, thereby inducing expression of caspase, prior to or concurrently with administration of the conjugate. In accordance with such some embodiments, apoptosis may be induced by any therapeutically acceptable means, such as a treatment selected from the group consisting of radiation therapy, hyperthermia, laser therapy, photodynamic therapy, chemotherapy, and cryosurgery, or targeted therapy, such as a small molecule tyrosine kinase inhibitor (TKI) or monoclonal antibody that targets tumor cells. The chemotherapeutic agent may be any chemotherapeutic agent known in the art, including those disclosed above, and may be the same as or different from the chemotherapeutic agent of the prodrug conjugate. In specific embodiments, including where the tumor or cancer has metastasized and/or is unidentifiable, the apoptotic inducing treatment may include targeted therapy, such as TKIs, antibodies, aptamers, or targeted nanoparticles, which target tumor cells.

In specific embodiments, apoptosis is induced by radiation therapy. As used herein, the term "radiation therapy" refers to all methods of radiation therapy, including external beam radiation therapy, sealed source ration therapy, and systemic radioisotope therapy. In some embodiments, the radiation is focused locally to the target site, such as to a tumor site. In some embodiments, radiation therapy is effected prior to administration of the prodrug conjugate. In any embodiments using radiation therapy, the radiation therapy may include gamma-knife radiation, cyber-knife radiation, and/or high intensity focused ultrasound radiation.

In some embodiments, the radiation therapy involves treatment with a low dose of radiation. In specific embodiments, an adult human subject is treated with radiation at a dose of up to about 70 Gy. In other embodiments, an adult human subject is treated with a single dose of radiation of up to about 35 Gy. In other embodiments, an adult human subject is treated with radiation at weekly doses of up to about 10 Gy.

As noted above, the prodrug conjugate may be administered by any route of administration. In specific embodiments, the prodrug conjugate is administered intravenously. The dose of prodrug conjugate administered will vary depending on the subject and the condition for which it is administered, and can be determined by someone of skill in the art. In some embodiments, the dose administered to a subject may be between about 1 mg/kg and about 100 mg/kg, including from about 5 mg/kg to about 75 mg/kg, such as from about 10 mg/kg to about 50 mg/kg, or greater. In specific embodiments, the prodrug conjugate exhibits lower toxicity than the chemotherapeutic agent alone, such that the dose administered may be higher than that which would be non-toxic for the chemotherapeutic agent alone.

In some embodiments, the prodrug conjugate is administered local to a target region, such as by local injection into a tumor site. In certain embodiments, this target region has already been treated with an apoptosis inducing treatment, as set forth above.

In some embodiments the subject is treated with a further apoptosis inducing treatment after the conjugate is administered. In such embodiments, the subsequent apoptosis inducing treatment may be the same as or identical to the previous apoptosis inducing treatment. Alternatively, the subsequent apoptosis inducing treatment may be different from the previous apoptosis inducing treatment. Possible differences include, but are not limited to, the type of treatment (e.g. radiation therapy, hyperthermia, laser therapy, photodynamic therapy, chemotherapy, cryosurgery, or targeted therapy), the chemotherapeutic agent or molecule for targeted therapy used; the radiation therapy used, and/or the dosage or duration of treatment, and any other variation of an apoptosis inducing treatment.

In specific embodiments, the methods described herein amplify apoptosis by the following process: Apoptosis is induced by an apoptosis inducing treatment, as disclosed above, resulting in expression of caspase. Prodrug conjugate is administered, and the caspase-cleavable peptide linker is cleaved by the caspase, releasing the chemotherapeutic agent. The chemotherapeutic agent induces apoptosis of additional cells, resulting in additional expression of caspase, resulting in the caspase-induced cleavage/activation of additional prodrug conjugate, resulting in amplified apoptosis. This amplification yields methods with high efficiency and specificity in killing target cells, such as target tumor cells. Moreover, this amplification effect can prolong the time interval between apoptosis inducing treatments and/or between administrations of doses of the prodrug conjugate. Thus, in some embodiments, this amplification effect may reduce the amount of chemotherapeutic agent needed to treat a certain number of cancer cells.

As noted above, the prodrug conjugate is inactive prior to cleavage of the caspase-cleavable peptide linker. Thus, the prodrug conjugate is not toxic (or apoptotic) to healthy cells. In specific embodiments, the methods described herein reduce damage to normal cells by about 10%, 20%, 30%, 40%, 50%, 60%, 70%, 80% or more, as compared with administration of the same chemotherapeutic agent in non-conjugated form.

Moreover, the apoptotic effect of the prodrug conjugate is selective to cells expressing caspase, e.g., cells undergoing apoptosis. Thus, once apoptosis is induced in a region of target cells (e.g., in target tissue), the methods described herein selectively and effectively induce apoptosis of other target cells, thereby, for example, treating cancer.

EXAMPLES

Example 1—Manufacturing Prodrug Maleimide-KGDEVD-PABC-Doxorubicin (SEQ ID NO: 10)

Maleimide is a functional group that binds endogenous albumin, and prolongs the plasma circulation of the prodrug conjugates described herein. The peptide linker KGDEVD (SEQ ID NO: 8) is specifically cleaved by caspase-3, -7, or -9.

In this example, ε-malcimidocaproylate and doxorubicin were bound to the amino group of the Lys side chain and the C-terminus of an AcKGDEVD peptide (SEQ ID NO: 33), respectively, with the doxorubicin being conjugated via a spacer molecule p-aminobezylcarbamate (PABC) to produce the prodrug conjugate maleimide-KGDEVD-PABC-doxorubicin (SEQ ID NO: 10) (see FIG. 1). After intravenous administration, the prodrug covalently binds to the circulating endogenous albumins and accumulates in tumor tissue. When radiation therapy is given, tumor cells express caspase-3 and/or -7, which cleave the KGDEVD linker (SEQ ID NO: 8) and release doxorubicin.

Figure 2:
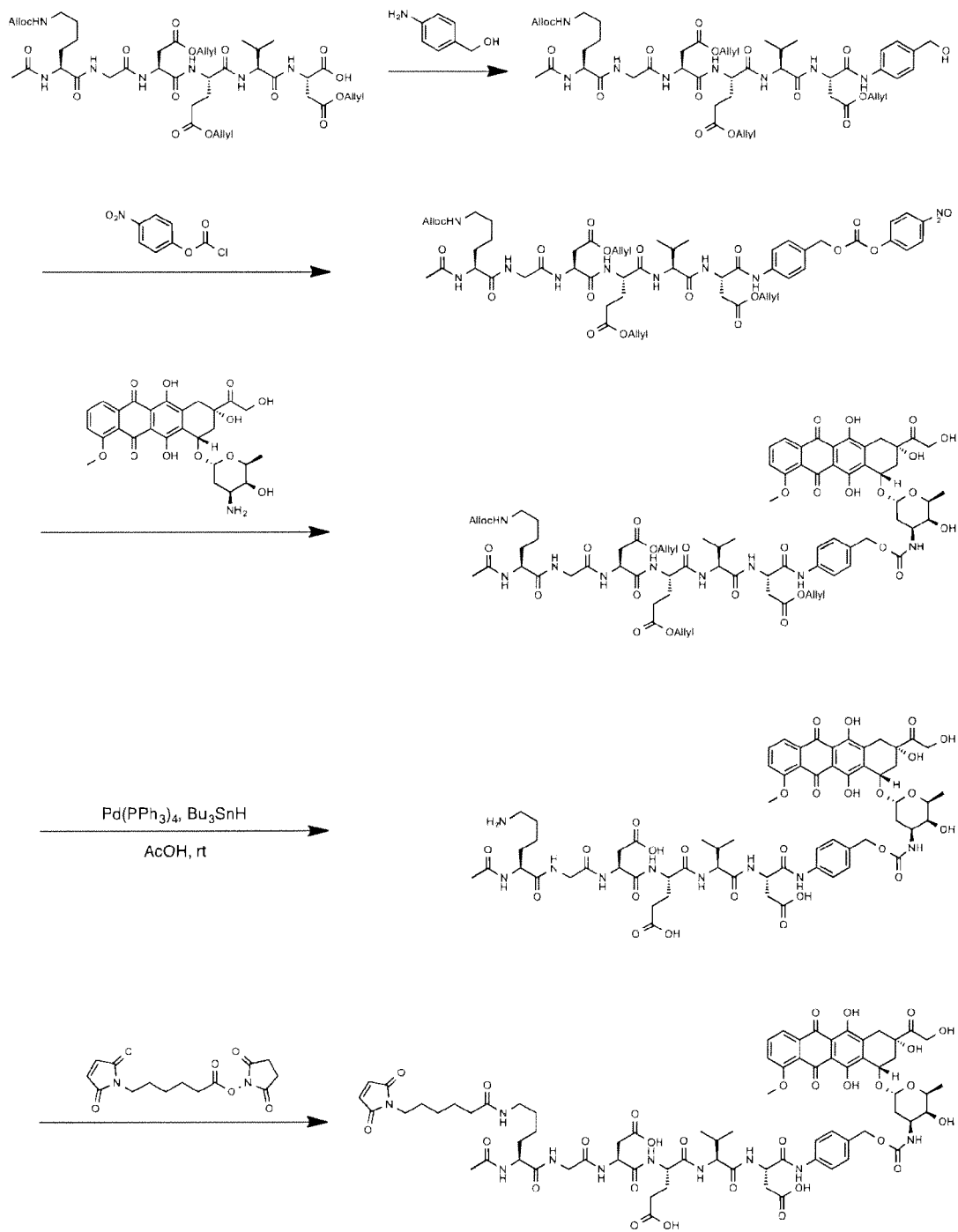
FIG. 2 depicts the synthetic scheme for obtaining a prodrug comprising one maleimide functional group, a peptide spacer containing Asp-Glu-Val-Asp sequence (SEQ ID NO: 4) (KGDEVD) (SEQ ID NO: 8), and doxorubicin as an active ingredient. In particular, doxorubicin and a peptide spacer are conjugated through p-aminobezylcarbamate (PABC) to obtain maleimide-KGDEVD-PABC-doxorubicin (SEQ ID NO: 10).

The maleimide-KGDEVD-PABC-doxorubicin (SEQ ID NO: 10) can be synthesized according to the process depicted in FIG. 2 as described below:

Ac-Lys(OAloc)-Gly-Asp(OAll)-Glu(OAll)-Val-Asp(OAll)-OH (SEQ ID NO: 34) (344 mg, 0.38 mmol), 4-aminobenzyl alcohol (2 eq), and EEDQ (SEQ ID NO: 35) (2 eq) is dissolved in anhydrous DMF (11 ml) and the reaction mixture is stirred at room temperature for 24 hours under inert atmosphere. The solution is concentrated under reduced pressure, and 10 volume of diethyl ether is added. The precipitate is collected by filtration and dried in vacuo to obtain Ac-Lys(OAloc)-Gly-Asp(OAll)-Glu(OAll)-Val-Asp(OAll)-PABOH (SEQ ID NO: 36) (322 mg, 84%). ESI-MS (m/z): 1035.7 [M+Na]+.

Ac-Lys(OAloc)-Gly-Asp(OAll)-Glu(OAll)-Val-Asp(OAll)-PABOH (SEQ ID NO: 36) (322 mg, 0.318 mmol) and 4-nitrophenyl chloroformate (1.2 eq) are dissolved in anhydrous $CH_2Cl_2$ (10 ml) under inert atmosphere. Then 2,6-lutidine (3 eq) is added to the reaction mixture and stirred at room temperature for 2 hours. Anhydrous DMF (2 ml) and additional 2,6-lutidine (2 eq) are added to the reaction mixture. After 24, 27, and 46 hours, 2,6-lutidine (4.75 eq) and 4-nitrophenyl chloroformate (1 eq) are added to the reaction mixture, respectively. After 84 hours, aqueous NaHCO3 is added to the reaction mixture and extracted with ethyl acetate (100 ml×3). The organic layer is washed with 0.5 M citric acid, aqueous $NaHCO_3$, and brine, subsequently. The obtained organic layer is dried by addition of anhydrous $NaSO_4$, filtered, and concentrated in vacuo. The concentrate is further purified with semi-preparative HPLC using a C18 reverse phase column (250 mm×22 mm) in a gradient system (Water and $CH_3CN$ with 0.1% TFA as an additive, $CH_3CN$ 20-53% over 30 min, 10 ml/min) to obtain Ac-Lys(OAloc)-Gly-Asp(OAll)-Glu(OAll)-Val-Asp(OAll)-PABC (SEQ ID NO: 37) (77 mg, 20.5%). ESI-MS (m/z): 1200.54 [M+Na]+.

Ac-Lys(OAloc)-Gly-Asp(OAll)-Glu(OAll)-Val-Asp(OAll)-PABC (SEQ ID NO: 37) (77 mg, 0.065 mmol) and doxorubicin HCl (1.2 eq) are dissolved in anhydrous DMF (8 ml). DIEA (5.4 eq) is added to the reaction mixture and stirred at room temperature for 16 hours under inert atmosphere. The solution is concentrated in vacuo and further purified with semi-preparative HPLC using a C18 reverse phase column (250 mm×22 mm) in a gradient system (Water and $CH_3CN$ with 0.1% TFA as an additive, $CH_3CN$ 20-100% over 50 min, 10 ml/min) to obtain Ac-Lys(OAloc)-Gly-Asp(OAll)-Glu(OAll)-Val-Asp(OAll)-PABC-doxorubicin (SEQ ID NO: 38) (red amorphous solid, 50 mg, 50%). ESI-MS (m/z): 1605.06 [M+Na]+.

Ac-Lys(OAloc)-Gly-Asp(OAll)-Glu(OAll)-Val-Asp(OAll)-PABC-doxorubicin (SEQ ID NO: 38) (50 mg, 0.032 mmol) and $Pd(PPh_3)_4$ (0.2 eq) are dissolved in anhydrous DMF (4 ml) under inert gas and degassed over 5 min. Then tributyltin hydride (17.3 eq) and acetic acid (20 eq) are added to the reaction mixture, and stirred at room temperature for 1 hour. The product is purified with semi-preparative HPLC using a C18 reverse phase column (250 mm×22 mm) in a gradient system (Water and $CH_3CN$ with 0.1% TFA as an additive, $CH_3CN$ 20-41% over 41 min, 10 ml/min) to obtain deprotected Ac-Lys-Gly-Asp-Glu-Val-Asp-PABC-doxorubicin (SEQ ID NO: 32) (red amorphous solid, 6 mg, 13.6%). ESI-MS (m/z): 1378.4 [M+Na]+.

Ac-Lys-Gly-Asp-Glu-Val-Asp-PABC-doxorubicin (SEQ ID NO: 32) (20 mg, 0.013 mmol) and N-(ϵ-maleimidocaproyloxy)succinimide ester (EMCS; 8.26 mg, 26.8 mol, 2 eq; Pierce, Rockford, Ill.) are dissolved in anhydrous DMF (1.5 ml; Sigma-Aldrich, St. Louis, Mo.) under inert gas. Then $Et_3N$ (4.64 µl, 2.5 eq; Sigma-Aldrich) is added to the reaction mixture and stirred at room temperature for 2 hours. The final product is purified with semi-preparative HPLC (Shimadzu, Kyoto, Japan) using an ODS-A 5 µm reverse phase semi-preparative column (150 mm×20 mm) in a gradient system (Water and $CH_3CN$ with 0.05% TFA as an additive, $CH_3CN$ 20-50% over 50 min, 8 ml/min) to obtain Ac-Lys(EMC)-Gly-Asp-Glu-Val-Asp-PABC-doxorubicin (SEQ ID NO: 39) (red amorphous solid, 16.7 mg, 73.6%). The peaks are monitored at 280 nm. The purity of the final products is confirmed by analytical HPLC (Agilent 1300 series, Agilent Technologies, Santa Clara, Calif.) using ODS-A 5 µm analytical column (150 mm×3 mm; YMC) in a gradient system (Water and $CH_3CN$ with 0.1% TFA as an additive, $CH_3CN$ 5-95%/5-30 min, 1 ml/min). The peaks are monitored under a UV detector (214 nm) and fluorescent detector (excitation 470 nm, emission 580 nm). The purity of the final compound is determined to be >95%. ESI-MS (m/z): 1593.3 [M+Na]+.

Example 2—Manufacturing Prodrug Maleimide-KGDEVD-PABC-Daunorubicin (SEQ ID NO: 11)

Figure 3:
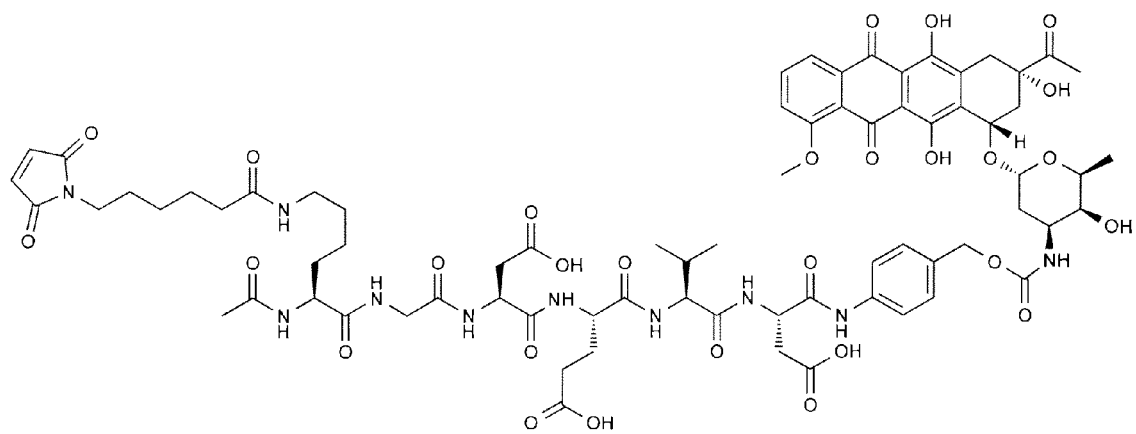
FIG. 3 depicts the chemical structure of maleimide-KGDEVD-PABC-daunorubicin (SEQ ID NO: 11).

The peptide prodrug of this example is similar to that of Example 1, but has daunorubicin as a chemotherapeutic agent (see FIG. 3).

Example 3—Manufacturing Prodrug Maleimide-KGDEVD-PABC-Paclitaxel (SEQ ID NO: 12)

Figure 4:
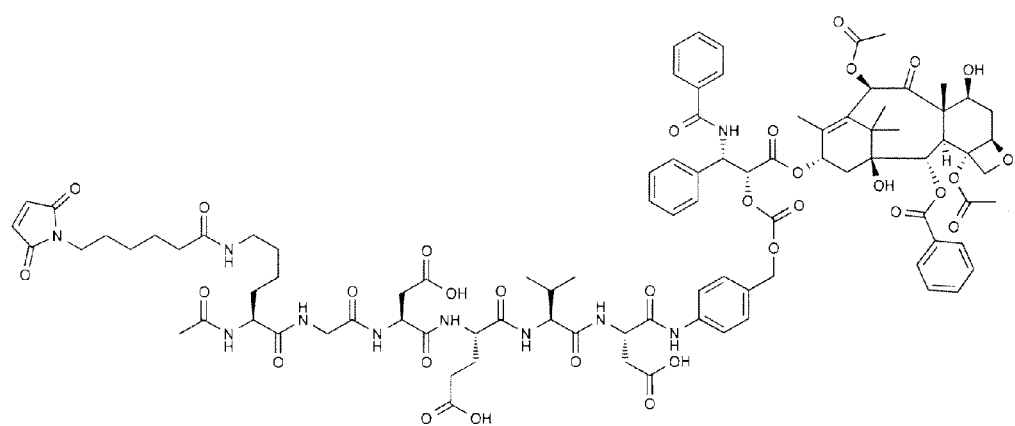
FIG. 4 depicts the chemical structure of maleimide-KGDEVD-PABC-paclitaxel (SEQ ID NO: 12).

The peptide prodrug of this example is similar to that of Example 1, but has paclitaxel as a chemotherapeutic agent (see FIG. 4).

Example 4—Manufacturing Prodrug Maleimide-KGDEVD-PABC-MMAE (SEQ ID NO: 13)

Figure 5:
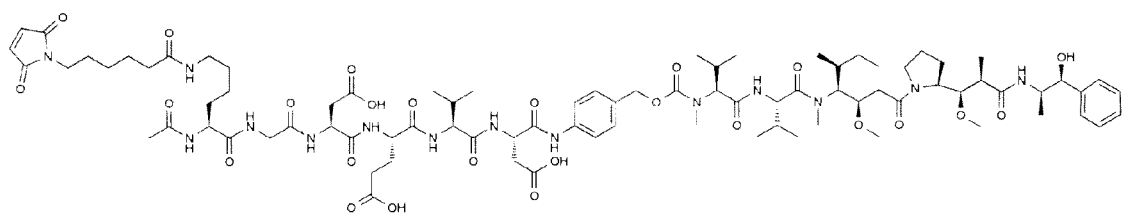
FIG. 5 depicts the chemical structure of maleimide-KGDEVD-PABC-MMAE (SEQ ID NO: 13).

The peptide prodrug of this example is similar to that of Example 1, but has MMAE (monomethyl auristatin E) as a chemotherapeutic agent (see FIG. 5).

Example 5—Manufacturing Prodrug Maleimide-DEVD-PABC-Doxorubicin (SEQ ID NO: 14)

Figure 6:
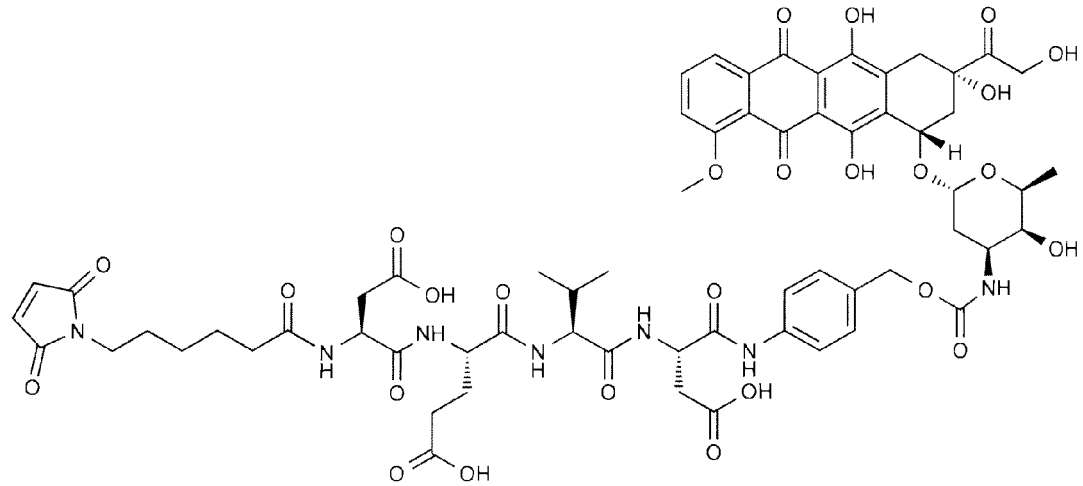
FIG. 6 depicts the chemical structure of maleimide-DEVD-PABC-doxorubicin (SEQ ID NO: 14).

The peptide prodrug of this example is similar to that of Example 1, but has DEVD (SEQ ID NO: 4) as a caspase-cleavable peptide linker (see FIG. 6). DEVD (SEQ ID NO: 4) is cleaved by caspase-3, -7, or -9.

Example 6—Manufacturing Prodrug: Maleimide-DEID-PABC-Doxorubicin (SEQ ID NO: 15)

Figure 7:
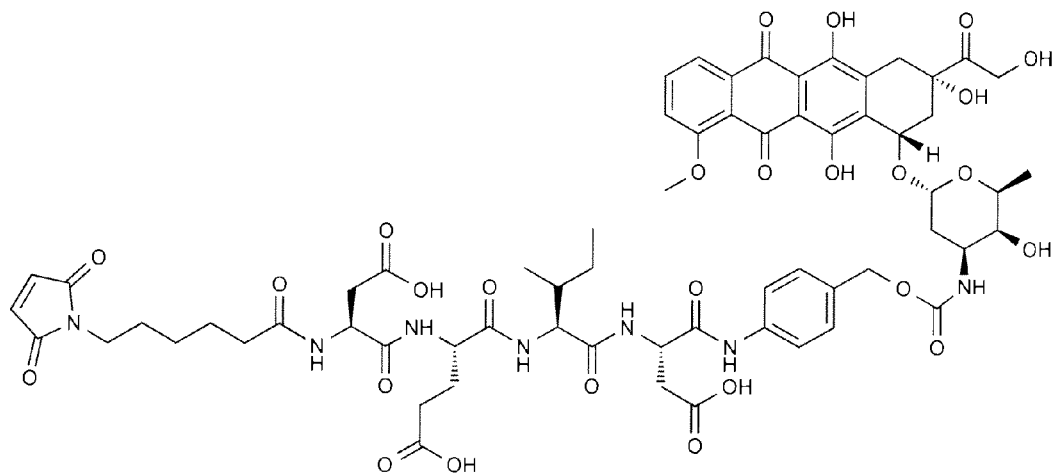
FIG. 7 depicts the chemical structure of maleimide-DEID-PABC-doxorubicin (SEQ ID NO: 15).

The peptide prodrug of this example is similar to that of Example 4, but has DEID (SEQ ID NO: 6) as a caspase-cleavable peptide linker (see FIG. 7). DEID (SEQ ID NO: 6) is cleaved by caspase-3, -7, or -9.

Example 7—Manufacturing Prodrug Maleimide-DLVD-PABC-Doxorubicin (SEQ ID NO: 16)

Figure 8:
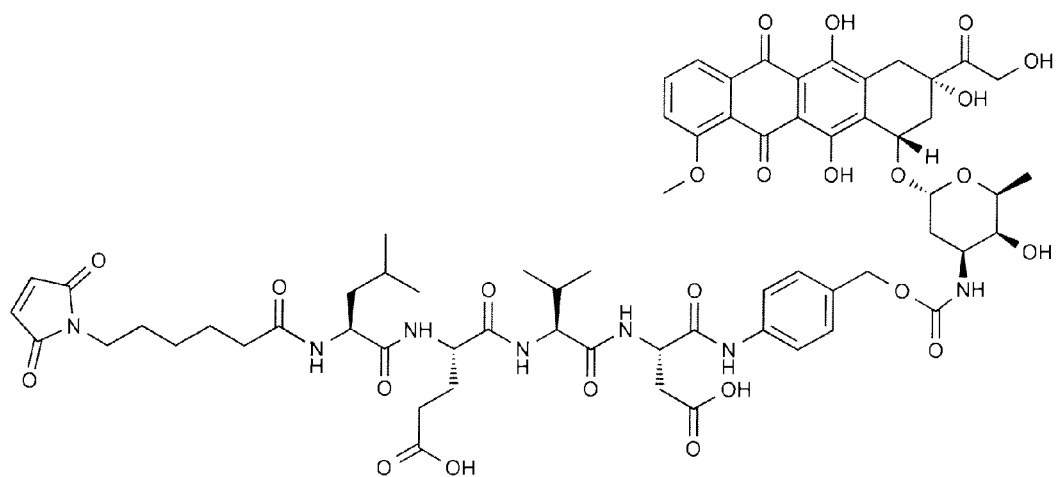
FIG. 8 depicts the chemical structure of maleimide-DLVD-PABC-doxorubicin (SEQ ID NO: 16).

The peptide prodrug of this example is similar to that of Example 4, but has DLVD (SEQ ID NO: 5) as a caspase-cleavable peptide linker (see FIG. 8). DLVD (SEQ ID NO: 5) is cleaved by caspase-3, -7, or -9.

Example 8—Manufacturing Prodrug Maleimide-DEVD-Doxorubicin (SEQ ID NO: 17) (without PABC)

Figure 9:
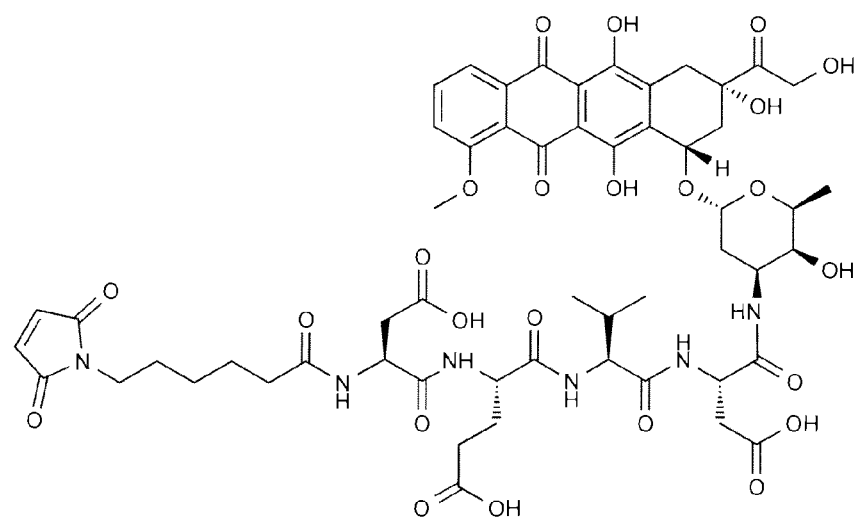
FIG. 9 depicts the chemical structure of maleimide-DEVD-doxorubicin (SEQ ID NO: 17).

The peptide prodrug of this example is similar to that of Example 4, but does not include the PABC spacer. In this example, the peptide linker is directly conjugated to the 3'-NH$_2$ of doxorubicin to produce the prodrug conjugate maleimide-DEVD-doxorubicin (SEQ ID NO: 17) (see FIG. 9).

Example 9—Manufacturing Prodrug Maleimide-DEVD-MMAE (SEQ ID NO: 29) (without PABC)

Figure 10:
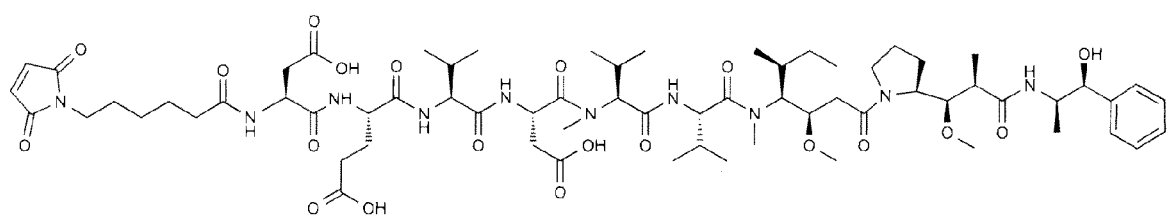
FIG. 10 depicts the chemical structure of maleimide-DEVD-MMAE (SEQ ID NO: 29).

The peptide prodrug of this example is similar to that of Example 1, but has MMAE (monomethyl auristatin E) as a chemotherapeutic agent (see FIG. 10).

Example 10—Manufacturing Prodrug: Pyridyldithiol-KGDEVD-PABC-Doxorubicin (SEQ ID NO: 18)

Figure 11:
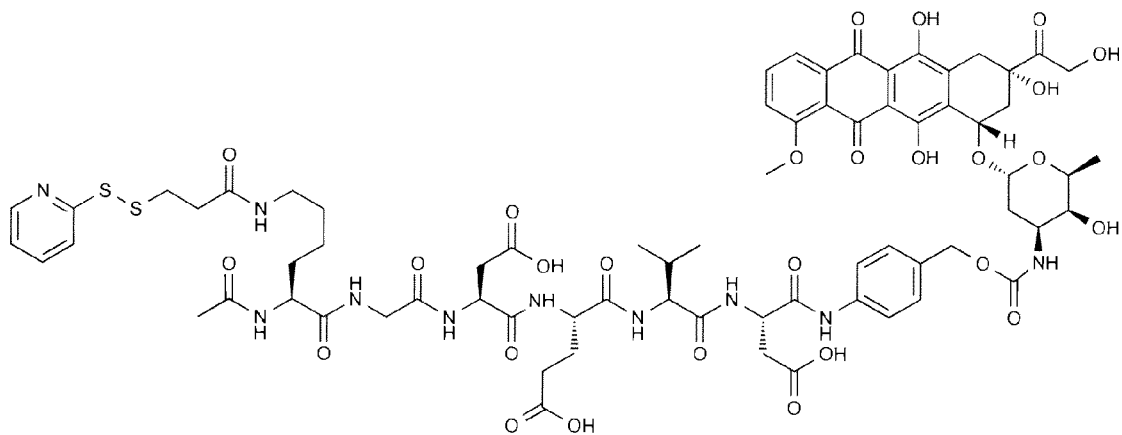
FIG. 11 depicts the chemical structure of pyridyldithiol-KGDEVD-PABC-doxorubicin (SEQ ID NO: 18).

The peptide prodrug of this example is similar to that of Example 1, but includes pyridyldithiol as the functional moiety and doxorubicin as the chemotherapeutic agent (see FIG. 11). The pyridyldithiol moiety bind binds endogenous albumin, and prolongs the plasma circulation of the prodrug conjugates. In this example, 3-(2-pyridyldithiol)propionate and doxorubicin are bound to the N- and C-terminus, respectively, of the KGDEVD peptide (SEQ ID NO: 8), which is cleaved by caspase-3, -7, or -9. As with the other prodrug conjugates exemplified above, the prodrug conjugate covalently binds to circulating endogenous albumin and accumulates at tumor sites. When apoptosis is induced and caspase-3 and/or -7 is expressed, the caspase clevable-peptide linker is cleaved, releasing the doxorubicin.

Example 11—Manufacturing Prodrug Oleate-KGDEVD-PABC-Doxorubicin (SEQ ID NO: 19)

Figure 12:
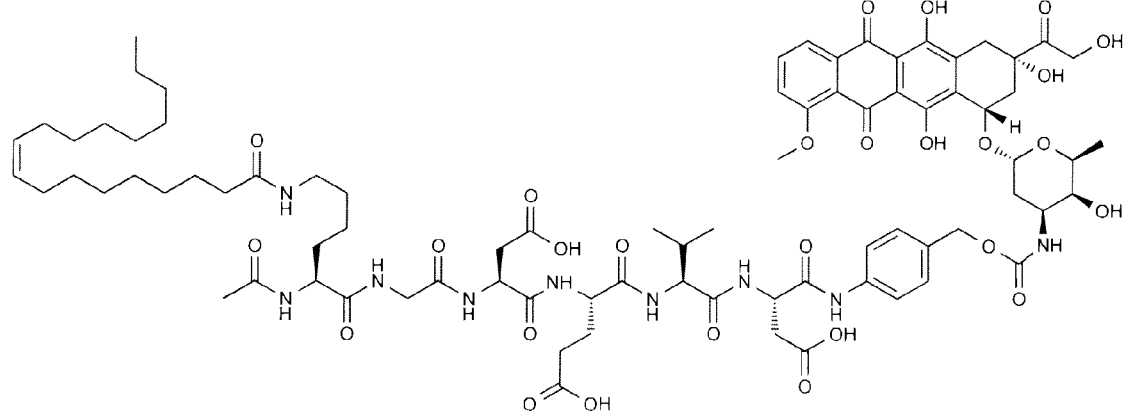
FIG. 12 depicts the chemical structure of oleate-KGDEVD-PABC-doxorubicin (SEQ ID NO: 19).

The peptide prodrug of this example is similar to that of Example 9, but includes oleate as the functional moiety (see FIG. 12). The oleate moiety bind binds endogenous albumin, and prolongs the plasma circulation of the prodrug conjugates.

Example 12—Manufacturing Prodrug Polyethylene Glycol-KGDEVD-PABC-Doxorubicin (SEQ ID NO: 20)

Figure 13:
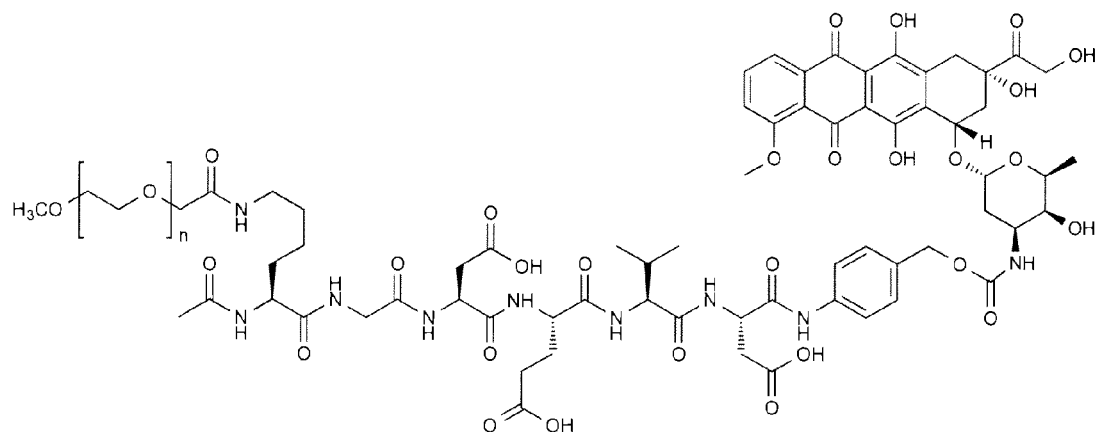
FIG. 13 depicts the representative chemical structure of PEG-KGDEVD-PABC-doxorubicin (SEQ ID NO: 20).

The peptide prodrug of this example is similar to that of Example 9, but includes polyethylene glycol as the functional moiety (see FIG. 13 for a representative structure). Due to the polyethylene glycol moiety, the prodrug conjugate circulates in the blood with a very long half-life and accumulates in the tumor, until caspase activation and release of the doxorubicin as described above.

Example 13—Manufacturing Prodrug Hyaluronan-KGDEVD-PABC-Doxorubicin (SEQ ID NO: 21)

Figure 14:
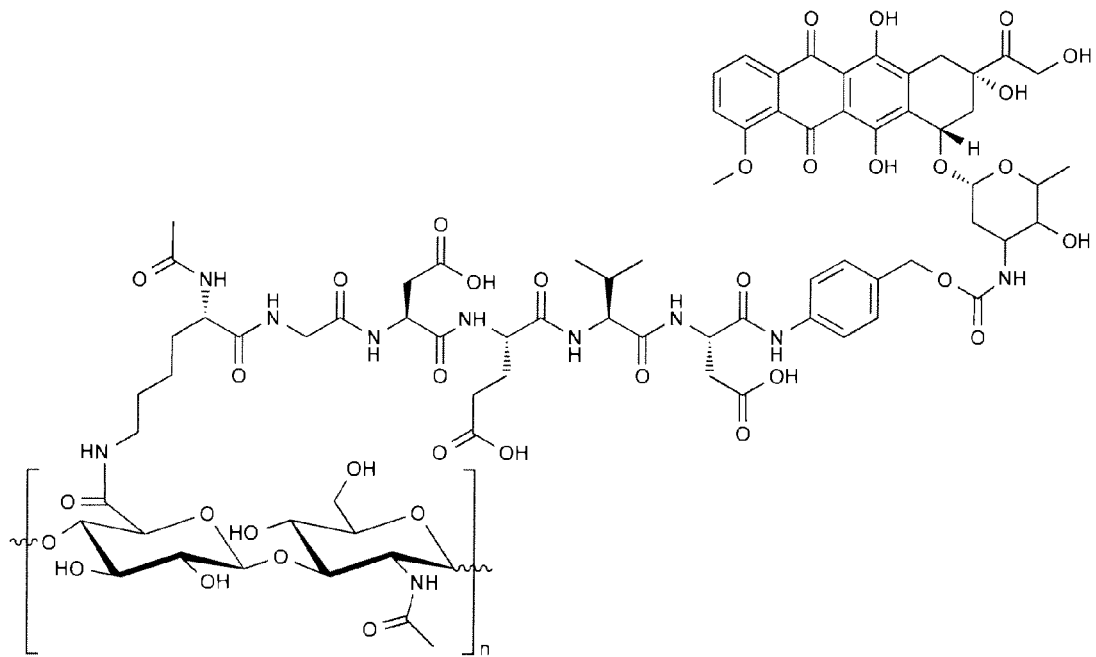
FIG. 14 depicts the representative chemical structure of hyaluronan-(KGDEVD-PABC-doxorubicin)$_n$ (SEQ ID NO: 21).

The peptide prodrug of this example is similar to that of Example 8, but includes hyaluronan as the functional moiety (see FIG. 14 for a representative structure). As illustrated in FIG. 14, several doxorubicin-peptide units can be conjugated to a single molecule of hyaluronic acid. After intravenous administration, the prodrug conjugate circulates in the blood with a very long half-life and accumulates in the tumor, until caspase activation and release of the doxorubicin as described above.

Example 14—Manufacturing Prodrug Folate-KGDEVD-PABC-Doxorubicin (SEQ ID NO: 22)

Figure 15:
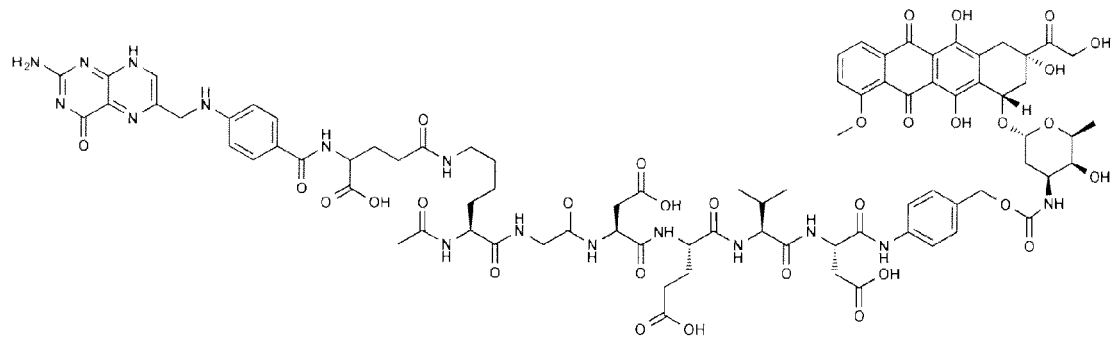
FIG. 15 depicts the chemical structure of Folate-KGDEVD-PABC-doxorubicin (SEQ ID NO: 22).

The peptide prodrug of this example is similar to that of Example 9, but includes folate as the functional moiety (see FIG. 15). Folate binds with folate receptors with high affinity, and so functions to target the prodrug conjugate to folate receptors present on tumor cells, which overexpress folate receptors, thereby leading to selective accumulation of the prodrug conjugate at tumor sites. When apoptosis is induced, the doxorubicin is released from the prodrug conjugate as discussed above.

Example 15—Manufacturing Prodrug RGDEVD-PABC-Doxorubicin

Figure 16:
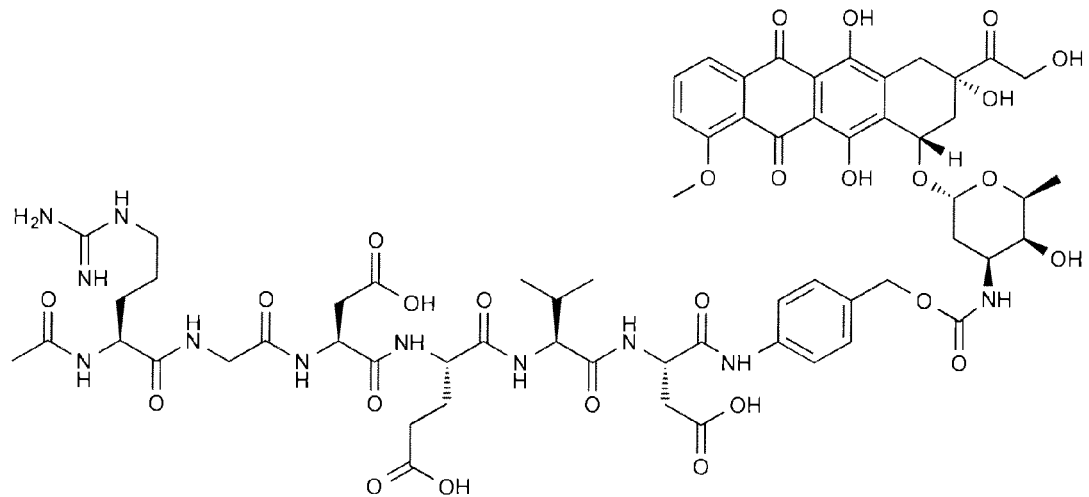
FIG. 16 depicts the chemical structure of RGDEVD-PABC-doxorubicin (SEQ ID NO: 23).
Figure 17:
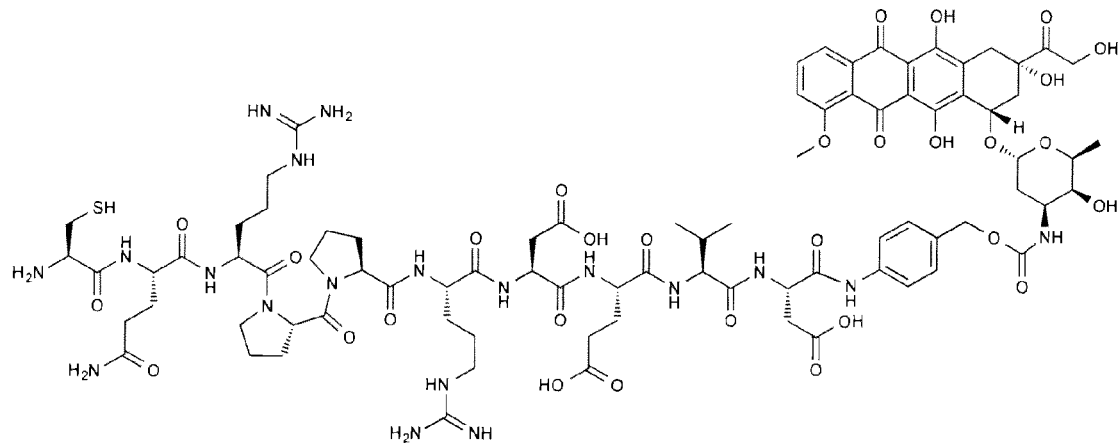
FIG. 17 depicts the chemical structure of cyclo(CRGDC) GGDEVD-PABC-doxorubicin (SEQ ID NO: 30).

In this example, the functional moiety and caspase-cleavable peptide linker together are comprised in the RGDEVD moiety (SEQ ID NO: 40), of which RGD is an integrin $\alpha_v\beta_3$ and/or $\alpha_v\beta_5$ targeting sequence and DEVD (SEQ ID NO: 4) is a caspase-cleavable peptide sequence (see FIG. 16 and FIG. 17). (The RGD moiety may be linear or cyclic). After intravenous administration, the prodrug is selectively accumulated in the tumor by binding to integrin $\alpha_v\beta_3$ and/or $\alpha_v\beta_5$, which is expressed on tumor endothelium and tumor cells. When apoptosis is induced, the doxorubicin is released from the prodrug conjugate as discussed above, by cleavage of the DEVD linker (SEQ ID NO: 4).

Example 16—Manufacturing Prodrug CQRPPRDEVD-PABC-Doxorubicin (SEQ ID NO: 24)

Figure 18:
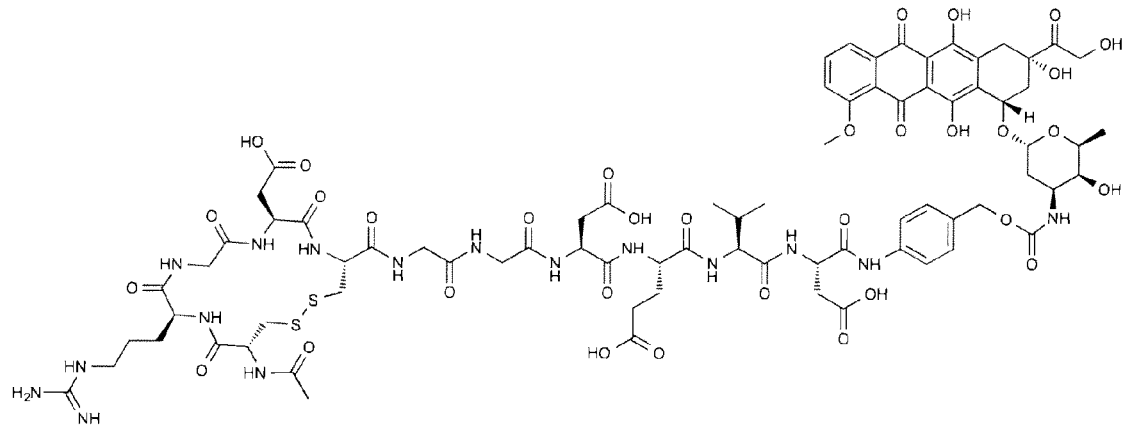
FIG. 18 depicts the chemical structure of CQRP-PRDEVD-PABC-doxorubicin (SEQ ID NO: 24).

In this example, the functional moiety and caspase-cleavable peptide linker together are comprised in the CQRPPRDEVD moiety (SEQ ID NO: 41), which includes a histone H1 targeting peptide sequence as well as a caspase-cleavable peptide sequence (see FIG. 18 for a representative structure). After administered intravenously, the prodrug is targeted to sites of apoptosis, since apoptotic cells express histone H1, where caspase that also is expressed by apoptotic cells cleaves the prodrug and releases the doxorubicin.

Example 17—Manufacturing Prodrug RGDEVD-MBA-Doxorubicin (SEQ ID NO: 25)

Figure 19:
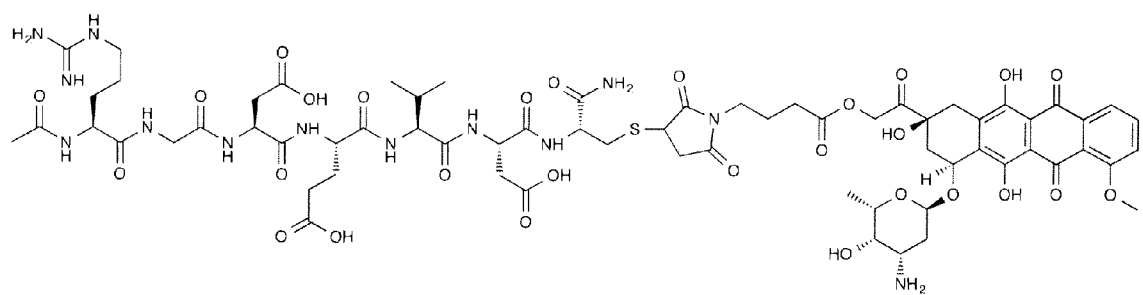
FIG. 19 depicts the chemical structure of RGDEVD-MBA-doxorubicin (SEQ ID NO: 25).

The peptide prodrug of this example is similar to that of Example 15 (see FIG. 19). In particular, the RGDEVD peptide (SEQ ID NO: 40) is connected to the 14-OH position of the doxorubicin to produce AcRGDEVD-MBA-doxorubicin (SEQ ID NO: 42).

The AcRGDEVD-MBA-doxorubicin (SEQ ID NO: 42) can be synthesized as described below:

14-Doxorubicinyl maleimidobutyrate ester is synthesized according to Meyer-Losic et al. for conjugation with the prepared peptides (Meyer-Losic, F., et al., J. Med. Chem., 2006, 49, 6908-16). Daunorubicin hydrochloride (100 mg, 177.3 µmol) is dissolved in a mixture of anhydrous methanol (3 ml) and anhydrous 1,4-dioxane (2.5 ml). Trimethyl orthoformate (89.2 µl, 815.6 µmol, 4.6 eq) is added followed by addition of bromine (15.7 µl, 306.8 µmol, 1.73 eq) at 11° C. and reacted for 2 hours under nitrogen. Propylene oxide (31.9 µl, 455.7 µmol, 2.57 eq) is added at 4° C. and reacted for 75 minutes. Then a mixture of acetone (8.6 ml) and 0.25 M hydrobromic acid (3 ml) is added, and reacted for 48 hours at room temperature. When the reaction is completed, the solution is diluted with distilled water (5 ml) and extracted with chloroform (10 ml×2). Saturated brine (5 ml) is added to the aqueous layer and the product is extracted into n-butanol until the aqueous layer is colorless. The collected n-butanol layer is concentrated at 35° C. in vacuo and precipitated in 10 volume of n-hexane to obtain 14-halodaunorubicin as red solid. m/z (ESI-MS): 562.0 [M+H]+ for 14-chlorodaunorubicin, 605.9 [M+H]+ for 14-bromodaunorubicin.

A suspension of 4-maleimidobutyric acid is prepared and 0.1 M sodium bicarbonate is slowly added during stirring. The resulting solution is stirred for 20 min and concentrated at 30° C. in vacuo. The concentrated solution is lyophilized to obtain sodium 4-maleimidobutyrate. The sodium 4-maleimidobutyrate (263 mg, 1.28 mmol) and 14-halodaunorubicin (138 mg, 237.2 mmol) are dissolved in acetone and refluxed under nitrogen for 4 hours. The solution is cooled and filtered. The remaining solid is washed with acetone and the filtrate is evaporated under vacuum. The red residue is dissolved in water with 0.1% trifluoroacetic acid (TFA) and subjected to semi-preparative reverse-phase HPLC (Shimadzu, Kyoto, Japan) using an ODS-A 5 µm semi-preparative column (150 mm×20 mm; YMC, Dinslaken, Germany) for further purification to obtain highly purified 14-doxorubicinyl maleimidobutyrate ester. A gradient system (Water and acetonitrile with 0.05% TFA as an additive) is used with a flow rate of 8 mL/min. Each step of the reaction is monitored using normal phase TLC (CH$_2$Cl$_2$:MeOH, 8:2). m/z (ESI-MS): 709.0 [M+H]+.

The 14-doxorubicinyl maleimidobutyrate ester and AcRGDEVDC-NH$_2$ (SEQ ID NO: 43) are dissolved in anhydrous DMF and reacted overnight at 4° C. The solution is precipitated in diisopropyl ether and the precipitate collected by filtration. The precipitate is washed three times with diisopropyl ether and dried in vacuo. The red solid is redissolved in water and subjected to a semi-preparative reverse-phase HPLC as mentioned above for further purification. Collected fractions are concentrated in reduced pressure and lyophilized to obtain the final product as a red powder. The purity of the final product is confirmed by analytical HPLC with UV detection at 214 nm and is determined to be >95%. m/z (ESI-MS): 1542.0 [M+H]+.

Example 18—Manufacturing Prodrug DEVD-Daunorubicin-RGDSC (SEQ ID NOS 26 and 27, Respectively)

Figure 20:
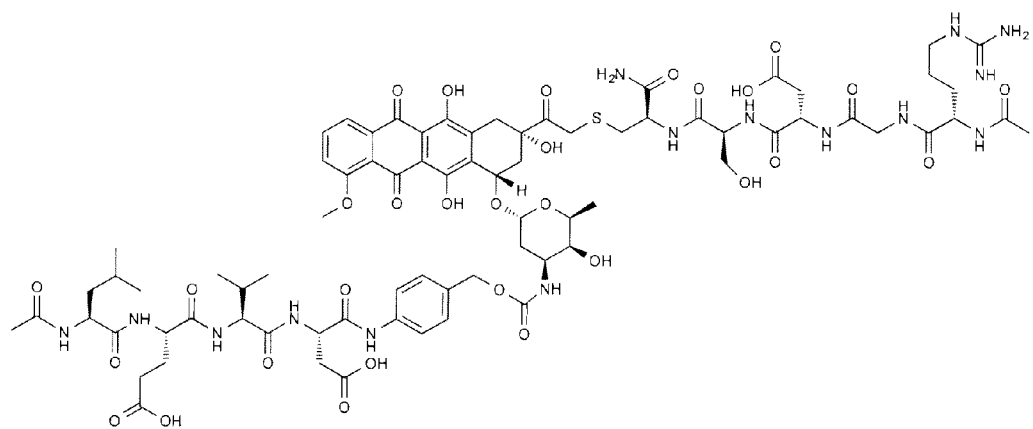
FIG. 20 depicts the chemical structure of DEVD-daunorubicin-RGDSC (SEQ ID NOS 26 and 27, respectively).

In this conjugate, the chemotherapeutic agent is conjugated to an integrin $\alpha_v\beta_3$ and/or $\alpha_v\beta_5$ targeting peptide sequence (RGD) and a caspase-cleavable peptide (see FIG. 20). (The RGD may be linear or cyclic). The RGDSC and DEVD peptides (SEQ ID NOS 35 and 4, respectively) were conjugated to the 14-CH$_3$ and 3'-NH$_2$ positions of the daunorubicin, respectively. After intravenous administration, the prodrug conjugate selectively accumulates in the tumor by binding to integrin $\alpha_v\beta_3$ and/or $\alpha_v\beta_5$, which is expressed on tumor endothelium and tumor cells, until caspase-induced cleavage which releases doxorubicin in a pharmaceutically active form.

Figure 21:
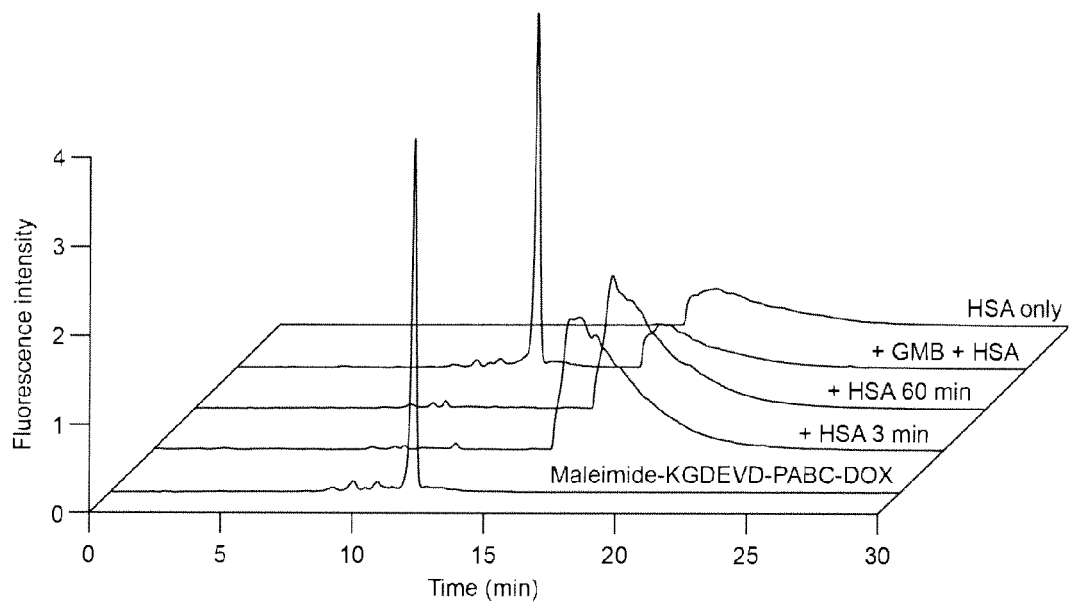
FIG. 21 shows HPLC monitored binding studies of maleimide-KGDEVD-PABC-doxorubicin (SEQ ID NO: 10) on commercially available human serum albumin (HSA).

Example 19—HPLC Monitored Binding Studies of Maleimide-KGDEVD-PABC-Doxorubicin (SEQ ID NO: 10) on Commercially Available Human Serum Albumin A human serum albumin (HSA) solution was prepared in PBS at final concentration of 700 µM. To the solution of HSA, maleimide-KGDEVD-PABC-doxorubicin (SEQ ID NO: 10) was added to a final concentration of 100 µM and incubated at room temperature. The samples were subjected to analytical HPLC (see FIG. 21).

The binding of the maleimide-KGDEVD-PABC-doxorubicin (SEQ ID NO: 10) conjugate to the HSA was accomplished within 3 minutes and only a trace amount of the unbound substance was detected. However, when HSA was preincubated with 4-maleimidobutyric acid, which is a small molecule containing a thiol-binding maleimide group, prior to incubation with maleimide-KGDEVD-PABC-doxorubicin (SEQ ID NO: 10), no binding of the maleimide-KGDEVD-PABC-doxorubicin (SEQ ID NO: 10) to the HSA was observed, even after 1 hour incubation, indicating that the binding of the maleimide-KGDEVD-PABC-doxorubicin (SEQ ID NO: 10) was specifically mediated by the maleimide group of the EMC moiety.

Figure 22:
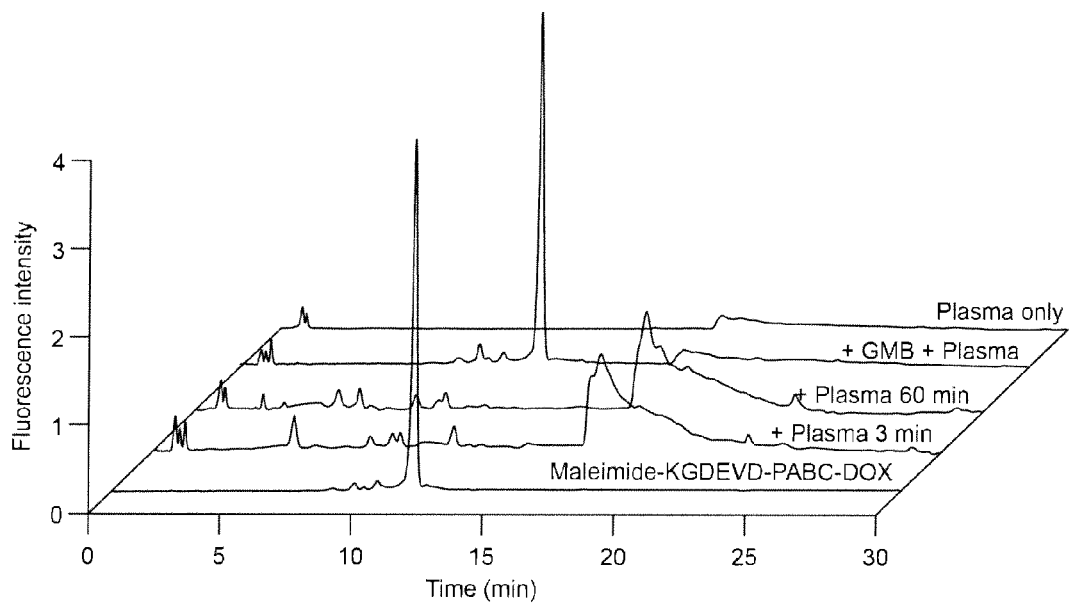
FIG. 22 shows HPLC monitored binding studies of maleimide-KGDEVD-PABC-doxorubicin (SEQ ID NO: 10) on human serum albumin in human plasma.

Example 20—HPLC Monitored Binding Studies of Maleimide-KGDEVD-PABC-Doxorubicin (SEQ ID NO: 10) on Human Serum Albumin in Human Plasma To human plasma samples, maleimide-KGDEVD-PABC-doxorubicin (SEQ ID NO: 10) was added to a final concentration of 100 µM and incubated at room temperature. Samples were subjected to analytical HPLC (sec FIG. 22).

The binding of the maleimide-KGDEVD-PABC-doxorubicin (SEQ ID NO: 10) to the serum albumin was accomplished within 3 minutes. However, when the plasma was preincubated with 4-maleimidobutyric acid, which is a small molecule containing a thiol-binding maleimide group, prior to incubation with maleimide-KGDEVD-PABC-doxorubicin (SEQ ID NO: 10), no evidence of binding of the maleimide-KGDEVD-PABC-doxorubicin (SEQ ID NO: 10) to the serum albumin was observed, even after 1 hour incubation, indicating that the binding of the maleimide-KGDEVD-PABC-doxorubicin (SEQ ID NO: 10) was specifically mediated by the maleimide group of the EMC moiety.

Example 21—HPLC Monitored Cleavage Studies of Human Serum Albumin-Bound Maleimide-KGDEVD-PABC-Doxorubicin (SEQ ID NO: 10) (HSA-KGDEVD-PABC-Doxorubicin (SEQ ID NO: 31)) by Recombinant Human Caspase-3

Figure 23:
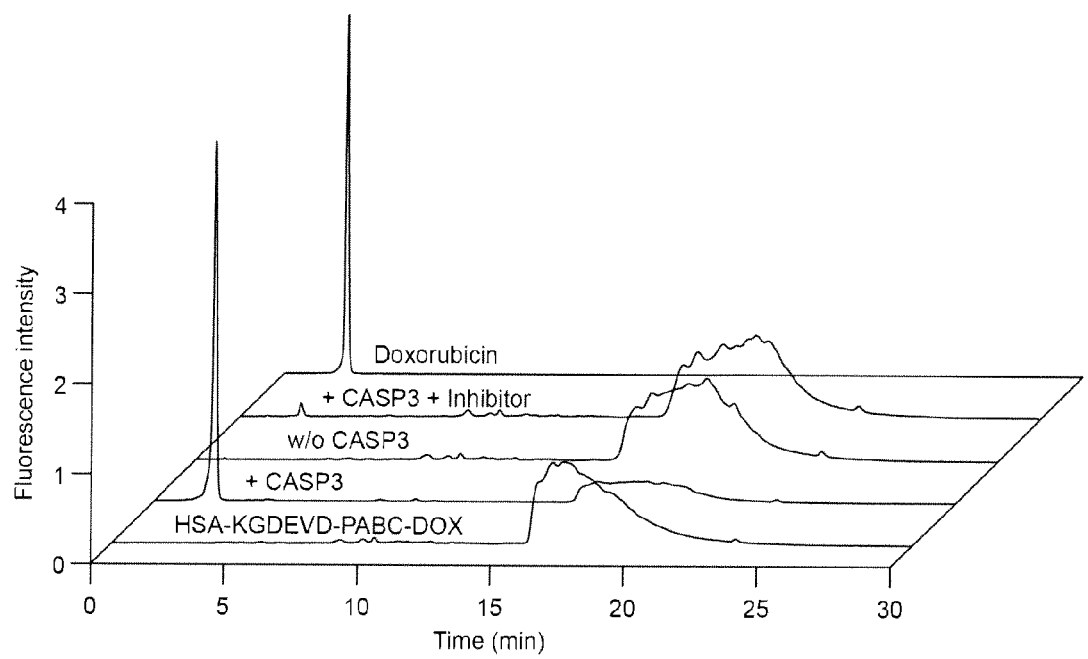
FIG. 23 shows HPLC monitored cleavage studies of human serum albumin-bound maleimide-KGDEVD-PABC-doxorubicin (SEQ ID NO: 10) (HSA-KGDEVD-PABC-doxorubicin (SEQ ID NO: 31)) by recombinant human caspase-3.

HSA-maleimide-KGDEVD-PABC-doxorubicin (SEQ ID NO: 28) was incubated with purified caspase-3 and subjected to HPLC analysis (see FIG. 23). The free doxorubicin was completely liberated from the HSA-maleimide-KGDEVD-PABC-doxorubicin (SEQ ID NO: 28) conjugate within 1 hour.

Example 22—The Concentration-Dependent In Vitro Anticancer Effect of HSA-KGDEVD-PABC-Doxorubicin (SEQ ID NO: 31) in the Presence or Absence of Recombinant Human Caspase-3

Figure 24:
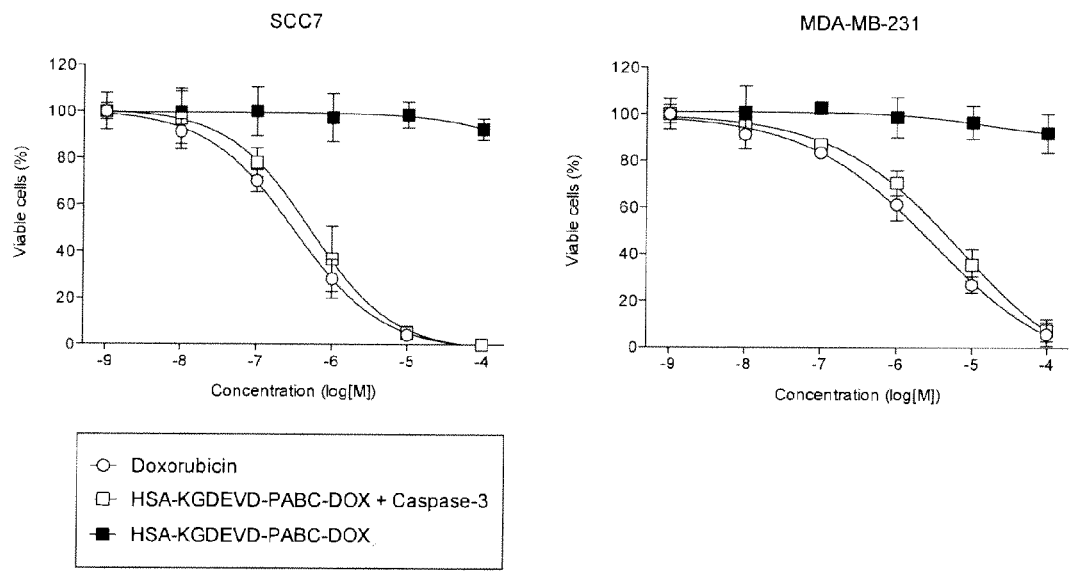
FIG. 24 shows the concentration-dependent in vitro anticancer effect of human serum albumin-bound maleimide-KGDEVD-PABC-doxorubicin (SEQ ID NO: 10) (HSA-KGDEVD-PABC-doxorubicin (SEQ ID NO: 31)) in the presence or absence of recombinant human caspase-3.

The HSA-Maleimide-KGDEVD-PABC-doxorubicin (SEQ ID NO: 28) conjugate did not show any noticeable cytotoxic effect up to 100 µM in both SCC7 and MDA-MB-231 cell when evaluated by an MTT assay (see FIG. 24). However, when the HSA-maleimide-KGDEVD-PABC-doxorubicin (SEQ ID NO: 28) was preincubated with purified caspase-3 prior to addition to the cells, it showed a similar degree of cytotoxicity as (unconjugated) doxorubicin on SCC7 and MDA-MB-231.

Figure 25:
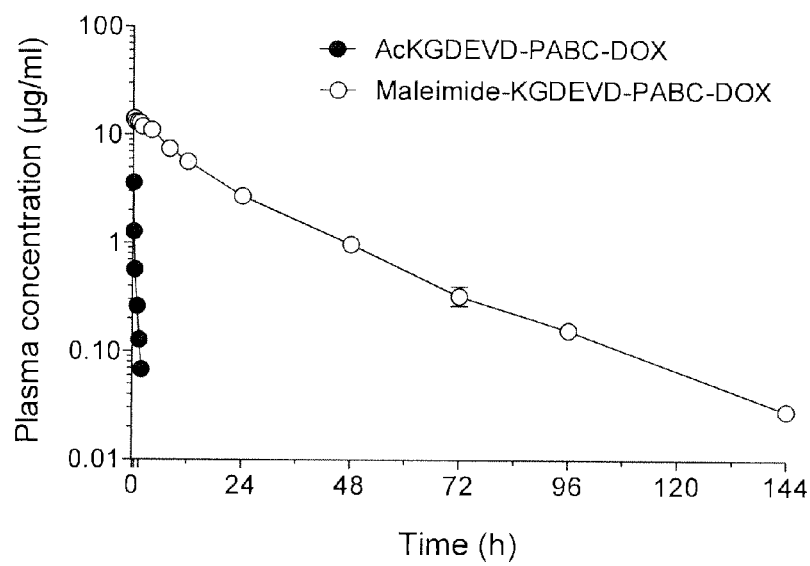
FIG. 25 shows the plasma concentration-time curve of doxorubicin in Sprague-Dawley rats administered maleimide-KGDEVD-PABC-doxorubicin (SEQ ID NO: 10) or AcKGDEVD-PABC-doxorubicin (SEQ ID NO: 32) intravenously.

Example 23—The Plasma Concentration-Time Curve of the Doxorubicin Content in Sprague-Dawley Rats Administered Maleimide-KGDEVD-PABC-Doxorubicin (SEQ ID NO: 10) or AcK-GDEVD-PABC-Doxorubicin (SEQ ID NO: 32) Intravenously The pharmacokinetic profile of the maleimide-KGDEVD-PABC-doxorubicin (SEQ ID NO: 10) and AcKGDEVD-PABC-doxorubicin (SEQ ID NO: 32) conjugates was determined after intravenous administration to Sprague-Dawley rats at a dose of molar equivalent to 1 mg/kg of doxorubicin (FIG. 25). Blood samples were collected at 5, 15, 30, 60, 90 minutes and then 2, 4, 8, 12, 24, 48, 72, 96, 144 hours post-injection (500 µl each). The collected blood samples were stabilized immediately with sodium citrate and centrifuged for 15 min at 2000×g in a refrigerated centrifuge to separated plasma. The plasma samples (200 µl) were transferred to a 96-well black microplate and the intrinsic fluorescence of doxorubicin was read at Ex 485 nm/Em 590 nm. A standard was prepared in fresh plasma and fluorescence was read as described above. The AcKGDEVD-PABC-doxorubicin (SEQ ID NO: 32) showed a terminal half-life of 30 minutes and the plasma concentration decreased below the detection limit (5 ng/ml) within 4 hours. On the other hand, maleimide-KGDEVD-PABC-doxorubicin (SEQ ID NO: 10) showed a significantly extended terminal half-life of more than 19 hours, and lasted more than 6 days in plasma after administration.

Figure 26:
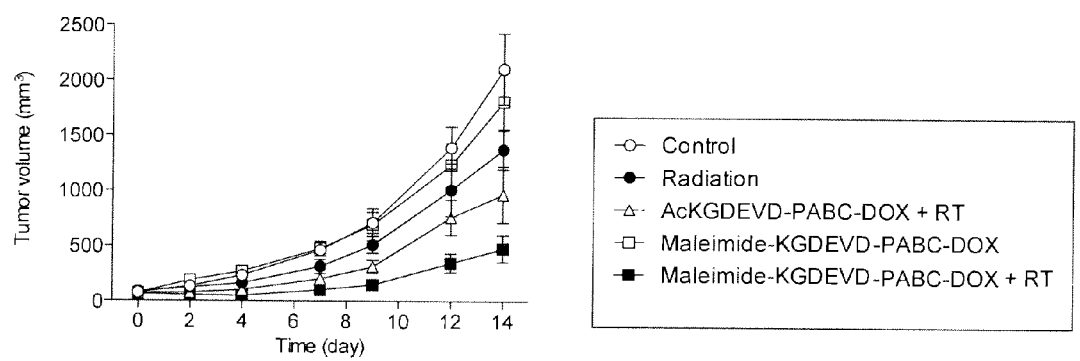
FIG. 26 shows the tumor growth profile of tumor-bearing animals administered maleimide-KGDEVD-PABC-doxorubicin (SEQ ID NO: 10) with or without initial exposure of radiation as compared to AcKGDEVD-PABC-DOX (SEQ ID NO: 32) with radiation.

Example 24—Tumor Growth Profile of Tumor-Bearing Animals Administered Maleimide-KGDEVD-PABC-Doxorubicin (SEQ ID NO: 10) with or without Initial Exposure of Radiation Tumor growth suppression by maleimide-KGDEVD-PABC-doxorubicin (SEQ ID NO: 10) was evaluated on SCC7-bearing C3H/HeN mice (see FIG. 26). Either maleimide-KGDEVD-PABC-doxorubicin (SEQ ID NO: 10) or AcKGDEVD-PABC-doxorubicin (SEQ ID NO: 32) were administered intravenously at a dose equivalent to 1 mg/kg of doxorubicin in molar aspect daily for seven days with observation for two weeks. For radiation treated groups, the tumors were treated with a single dose of 4 Gy linear X-ray at the first day of drug administration. The maleimide-KGDEVD-PABC-doxorubicin (SEQ ID NO: 10) itself showed a tumor suppression effect as shown by similar tumor growth when compared to the control group. When the maleimide-KGDEVD-PABC-doxorubicin (SEQ ID NO: 10) was combined with a single dose of radiation, a sufficient anticancer effect was observed. The maleimide-KGDEVD-PABC-doxorubicin (SEQ ID NO: 10) showed a more superior tumor suppression effect than AcKGDEVD-PABC-doxorubicin (SEQ ID NO 32).

Figure 27:
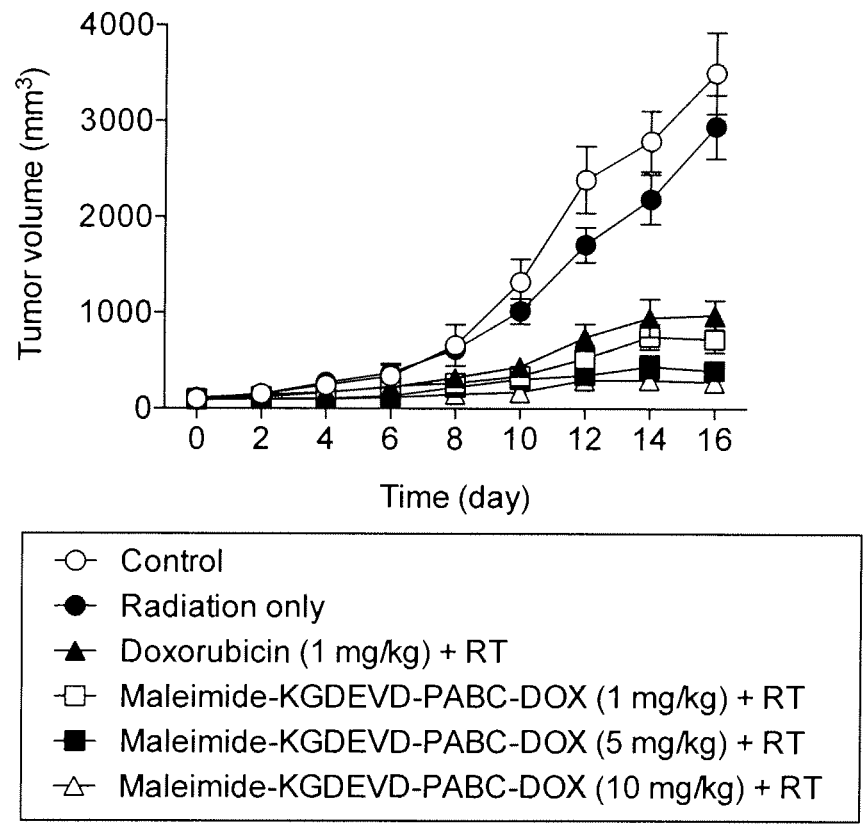
FIG. 27 shows the tumor growth profile of tumor-bearing animals administered different doses of maleimide-KGDEVD-PABC-doxorubicin (SEQ ID NO: 10) or doxorubicin and exposed to radiation with the initial dosing.

Example 25—Tumor Growth Profile of Tumor-Bearing Animals Administered Different Doses of Maleimide-KGDEVD-PABC-Doxorubicin (SEQ ID NO: 10) or Doxorubicin and Exposed to Radiation with the Initial Dosing Tumor growth suppression by maleimide-KGDEVD-PABC-doxorubicin (SEQ ID NO: 10) was evaluated on SCC7-bearing C3H/HeN mice (see FIG. 27). Maleimide-KGDEVD-PABC-doxorubicin (SEQ ID NO: 10) (1, 5, or 10 mg/kg molar equivalent of doxorubicin) or doxorubicin (1 mg/kg) was administered intravenously every other day for two weeks. The tumors were treated with a single dose of 4 Gy linear X-ray at the first day of drug administration. The maleimide-KGDEVD-PABC-doxorubicin (SEQ ID NO: 10) showed a dose-dependent anti-tumor effect and showed a superior tumor suppression effect as compared to free doxorubicin when administered in an equivalent dose.

Example 26—The Plasma Concentration-Time Curves of the Doxorubicin Content in Cynomolgus Monkeys Administered Maleimide-KGDEVD-PABC-Doxorubicin (SEQ ID NO: 10) and AcKGDEVD-PABC-Doxorubicin Intravenously (SEQ ID NO: 32)

Figure 28:
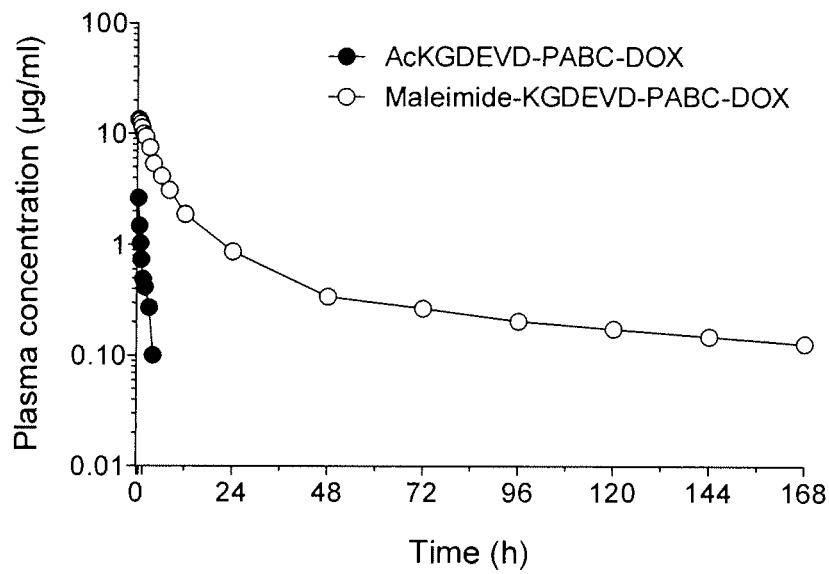
FIG. 28 shows the plasma concentration profiles of doxorubicin in cynomolgus monkeys administered Maleimide-KGDEVD-PABC-Doxorubicin (SEQ ID NO: 10) or AcK-GDEVD-PABC-Doxorubicin (SEQ ID NO: 32) intravenously.

The pharmacokinetic profiles of the maleimide-KGDEVD-PABC-doxorubicin (SEQ ID NO: 10) and AcK-GDEVD-PABC-doxorubicin (SEQ ID NO: 32) conjugates were determined after intravenous administration to Cynomolgus monkeys at a dose of molar equivalent to 1 mg/kg of doxorubicin (FIG. 28). Blood samples were collected at 15, 30, 45, 60, 90 minutes and then 2, 3, 4, 6, 8, 12, 24, 48, 72, 96, 120, 144, 168 hours post-injection (500 µl each). The collected blood samples were stabilized immediately with sodium citrate and centrifuged for 15 min at 2000×g in a refrigerated centrifuge to separate the plasma. The plasma samples (200 µl) were transferred to a 96-well black microplate and the intrinsic fluorescence of doxorubicin was read at Ex 485 nm/Em 590 nm. A standard was prepared in fresh plasma and the fluorescence was read as described above. The AcKGDEVD-PABC-doxorubicin (SEQ ID NO: 32) showed a terminal half-life of 1 hour and the plasma concentration decreased below the detection limit (5 ng/ml) within 6 hours. On the other hand, maleimide-KGDEVD-PABC-doxorubicin (SEQ ID NO: 10) showed a significantly extended terminal half-life of more than 106 hours, and the plasma concentration was detectable for more than 7 days after administration.

What is claimed is:

1. A chemotherapeutic prodrug conjugate comprising:
   (i) an albumin-binding moiety that prolongs plasma circulation of the conjugate, joined directly or through a linker to
   (ii) a caspase-cleavable peptide linker, wherein the four C-terminal amino acid residues of the caspase-cleavable peptide linker are selected from Asp-Xaa-Xaa-Asp (SEQ ID NO:1), Leu-Xaa-Xaa-Asp (SEQ ID NO:2), and Val-Xaa-Xaa-Asp (SEQ ID NO:3), where Xaa represents any amino acid residue, joined directly or through a linker to
   (iii) a chemotherapeutic agent.

2. The conjugate of claim 1, wherein the albumin-binding moiety is selected from the group consisting of maleimide, N-hydroxysuccinimide ester, halogenacetamide, halogenacetate, aziridine, disulfide, acetylene, pyridylthiol, oleate, and vinylcarbonyl.

3. The conjugate of claim 1, wherein the functional albumin-binding moiety is maleimide.

4. The conjugate of claim 1, wherein the caspase-cleavable peptide linker is cleavable by a caspase selected from the group consisting of caspase-3, caspase-7, and caspase-9.

5. The conjugate of claim 1, wherein the four C-terminal amino acid residues of the caspase-cleavable peptide linker are selected from the group consisting of Asp-Glu-Val-Asp (SEQ ID NO:4), Asp-Leu-Val-Asp (SEQ ID NO:5) Asp-Glu-Ile-Asp (SEQ ID NO:6), and Leu-Glu-His-Asp (SEQ ID NO:7).

6. The conjugate of claim 5, wherein the six C-terminal amino acid residues of the caspase-cleavable peptide linker consist of Lys-Gly-Asp-Glu-Val-Asp (SEQ ID NO:8).

7. The conjugate of claim 1, wherein the chemotherapeutic agent induces apoptosis of tumor cells.

8. The conjugate of claim 1, wherein the chemotherapeutic agent is selected from the group consisting of anthracyclines, antibiotics, alkylating agents, platinum-based agents, antimetabolites, topoisomerase inhibitors, and mitotic inhibitors.

9. The conjugate of claim 1, wherein the chemotherapeutic agent is selected from the group consisting of doxorubicin, daunorubicin, epirubicin, idarubicin, valrubicin, and derivatives thereof.

10. The conjugate of claim 1, wherein the chemotherapeutic agent is selected from the group consisting of actinomycin-D, bleomycin, mitomycin-C, calicheamicin, and derivatives thereof.

11. The conjugate of claim 1, wherein the chemotherapeutic agent is selected from the group consisting of cyclophosphamide, mechlorethamine, uramustine, melphalan, chlorambucil, ifosfamide, bendamustine, carmustine, lomustine, streptozocin, busulfan, dacarbazine, temozolomide, thiotepa, altretamine, duocarmycin, cisplatin, carboplatin, nedaplatin, oxaliplatin, satraplatin, triplatin tetranitrate, 5-fluorouracil, 6 mercaptopurine, capecitabine, cladribine, clofarabine, cystarbine, floxuridine, fludarabine, gemcitabine, hydroxyurea, methotrexate, pemetrexed, pentostatin, thioguanine, camptothecin, topotecan, irinotecan, etoposide, teniposide, mitoxantrone, paclitaxel, docetaxel, izabepilone, vinblastine, vincristine, vindesine, vinorelbine, estramustine, maytansine, DM1 (mertansine), DM4, dolastatin, auristatin E, auristatin F, monomethyl auristatin E, monomethyl auristatin F, and derivatives thereof.

12. The conjugate of claim 1, wherein the albumin-binding is maleimide, the caspase-cleavable peptide linker has an amino acid sequence consisting of Lys-Gly-Asp-Glu-Val-Asp (SEQ ID NO:8), and the chemotherapeutic agent is doxorubicin.

13. The conjugate of claim 1, selected from the group consisting Maleimide-KGDEVD-PABC-Doxorubicin (SEQ ID NO: 10), Maleimide-KGDEVD-PABC-Daunorubicin (SEQ ID NO: 11), Maleimide-KGDEVD-PABC-Paclitaxel (SEQ ID NO: 12), Maleimide-KGDEVD-PABC-MMAE (SEQ ID NO: 13), Maleimide-DEVD-PABC-Doxorubicin (SEQ ID NO: 14), Maleimide-DEID-PABC-Doxorubicin (SEQ ID NO: 15), Maleimide-DLVD-PABC-Doxorubicin (SEQ ID NO: 16), Maleimide-DEVD-Doxorubicin (SEQ ID NO: 17), Maleimide-DEVD-MMAE (SEQ ID NO: 29), Pyridyldithiol-KGDEVD-PABC-Doxorubicin (SEQ ID NO: 18), Oleate-KGDEVD-PABC-Doxorubicin (SEQ ID NO: 19), and HSA-Maleimide-KGDEVD-PABC-Doxorubicin (SEQ ID NO: 28).

14. A chemotherapeutic prodrug conjugate comprising:
   (i) a caspase-cleavable peptide, wherein the four C-terminal amino acid residues of the caspase-cleavable peptide linker are selected from Asp-Xaa-Xaa-Asp (SEQ ID NO:1), Leu-Xaa-Xaa-Asp (SEQ ID NO:2), and Val-Xaa-Xaa-Asp (SEQ ID NO:3), where Xaa represents any amino acid residue, joined directly or through a linker to
   (ii) daunorubicin, joined directly or through a linker at its 14-CH$_3$ to
   (iii) an albumin-binding moiety that prolongs plasma circulation of the conjugate.

15. A composition comprising the conjugate of claim 1 or claim 14 and a pharmaceutically acceptable carrier.

16. The composition of claim 1 or claim 14, formulated for intravenous administration.

17. A method of amplifying apoptosis in tumor cells in a subject comprising:
    inducing apoptosis in tumor cells thereby inducing expression of caspase; and
    administering to the subject a conjugate according to claim 1 or claim 14.

18. The method of claim 17, wherein apoptosis is induced before and, optionally, after, the conjugate is administered.

19. The method of claim 17, wherein the apoptosis is induced by a treatment selected from the group consisting of radiation, hyperthermia, laser therapy, photodynamic therapy, chemotherapy, and cryosurgery.

20. The method of claim 17, wherein the apoptosis is induced by treatment by a targeted therapy using an agent that targets tumor cells.

21. The method of claim 17, wherein the apoptosis is induced by treatment with a chemotherapeutic agent selected from the group consisting anthracyclines, antibiotics, alkylating agents, platinum-based agents, antimetabolites, topoisomerase inhibitors, and mitotic inhibitors.

22. The method of claim 17, wherein the apoptosis is induced by radiation therapy.

23. The method of claim 22, wherein the radiation therapy is effected before the conjugate is administered.

24. The method of claim 22, wherein the radiation therapy is selected from the group consisting of gamma-knife radiation, cyber-knife radiation, and high intensity focused ultrasound radiation.

25. The method of claim 22, wherein the radiation is applied at a dose of up to about 70 Gy.

26. The method of claim 22, wherein the radiation is applied as a single dose of up to about 35 Gy.

27. The method of claim 22, wherein the radiation therapy is applied at weekly doses of up to about 10 Gy.

28. The method of claim 17, wherein the conjugate is administered intravenously.

29. A method of amplifying apoptosis in tumor cells in a subject, comprising administering a conjugate according to claim 1 to a subject in need thereof who has been treated with a first apoptosis inducing treatment effective to induce expression of caspase.

30. The method of claim 29, wherein the apoptosis inducing treatment is selected from a group consisting of radiation, hyperthermia, laser therapy, photodynamic therapy, chemotherapy, and cryosurgery.

31. The method of claim 29, wherein the apoptosis inducing treatment is targeted therapy using an agent that targets tumor cells.

32. The method of claim 29, wherein the apoptosis is induced treatment with a chemotherapeutic agent selected from the group consisting of anthracyclines, antibiotics, alkylating agents, platinum-based agents, antimetabolites, topoisomerase inhibitors, and mitotic inhibitors.

33. The method of claim 30, wherein the apoptosis inducing treatment is radiation therapy.

34. The method of claim 29, further comprising, after administering the conjugate, treating the subject with a second apoptosis inducing treatment effective to induce expression of caspase.

35. The method of claim 34, wherein the second apoptosis inducing treatment is the same as the first apoptosis inducing treatment.

36. The method of claim 34, wherein the second apoptosis inducing treatment is different from the first apoptosis inducing treatment.

37. A method of treating cancer in a subject in need thereof comprising:
    treating the subject with an apoptosis inducing treatment effective to induce expression of caspase; and
    administering to the subject a conjugate according to claim 1.

38. The method of claim 37, wherein the apoptosis inducing treatment is effected before the conjugate is administered.

39. The method of claim 37, wherein the apoptosis inducing treatment is selected from a group consisting of radiation, hyperthermia, laser therapy, photodynamic therapy, chemotherapy, and cryosurgery.

40. The method of claim 37, wherein the apoptosis inducing treatment is targeted therapy using an agent that targets the cancer.

41. The method of claim 37, wherein the apoptosis is induced treatment with a chemotherapeutic agent selected from the group consisting of anthracyclines, antibiotics, alkylating agents, platinum-based agents, antimetabolites, topoisomerase inhibitors, and mitotic inhibitors.

42. The method of claim 37, wherein the apoptosis inducing treatment is radiation therapy.

43. A method of treating cancer comprising administering a conjugate according to claim 1 to a subject in need thereof who has been treated with a first apoptosis inducing treatment effective to induce expression of caspase.

44. The method of claim 43, wherein the apoptosis inducing treatment is selected from a group consisting of radiation, hyperthermia, laser therapy, photodynamic therapy, chemotherapy, and cryosurgery.

45. The method of claim 43, wherein the apoptosis inducing treatment is targeted therapy using an agent that targets the cancer.

46. The method of claim 43, wherein the apoptosis is induced treatment with a chemotherapeutic agent selected from the group consisting of anthracyclines, antibiotics, alkylating agents, platinum-based agents, antimetabolites, topoisomerase inhibitors, and mitotic inhibitors.

47. The method of claim 43, wherein the apoptosis inducing treatment is radiation therapy.

48. The method of claim 43, further comprising, after administering the conjugate, treating the subject with a second apoptosis inducing treatment effective to induce expression of caspase.

49. The method of claim 48, wherein the second apoptosis inducing treatment is the same as the first apoptosis inducing treatment.

50. The method of claim 48, wherein the second apoptosis inducing treatment is different from the first apoptosis inducing treatment.

* * * * *